(12) United States Patent
Kapsner et al.

(10) Patent No.: US 9,993,469 B2
(45) Date of Patent: *Jun. 12, 2018

(54) COMBINATION THERAPY COMPRISING OXAZOLIDINONE-QUINOLONES FOR USE IN TREATING BACTERIAL INFECTIONS

(71) Applicant: Morphochem Aktiengesellschaft Für Kombinatorische Chemie, München (DE)

(72) Inventors: Thomas Kapsner, Gröbenzell (DE); Axel Dalhoff, Wuppertal (DE)

(73) Assignee: Morphochem Aktiengesellschaft Für Kombinatorishe Chemie, München (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/894,408

(22) PCT Filed: May 28, 2014

(86) PCT No.: PCT/EP2014/001450
§ 371 (c)(1),
(2) Date: Nov. 27, 2015

(87) PCT Pub. No.: WO2014/191109
PCT Pub. Date: Dec. 4, 2014

(65) Prior Publication Data
US 2016/0113921 A1 Apr. 28, 2016

(30) Foreign Application Priority Data
May 28, 2013 (EP) .................................. 13002761

(51) Int. Cl.
| | |
|---|---|
| *A61K 31/4709* | (2006.01) |
| *A61K 31/665* | (2006.01) |
| *A61K 31/496* | (2006.01) |
| *A61K 31/43* | (2006.01) |
| *A61K 31/546* | (2006.01) |
| *A61K 31/407* | (2006.01) |
| *A61K 31/5377* | (2006.01) |
| *A61K 31/7036* | (2006.01) |
| *A61K 31/65* | (2006.01) |
| *A61K 38/12* | (2006.01) |
| *A61K 38/14* | (2006.01) |
| *A61K 45/06* | (2006.01) |
| *A61K 31/4375* | (2006.01) |
| *A61K 31/675* | (2006.01) |
| *A61K 35/12* | (2015.01) |

(52) U.S. Cl.
CPC ........ *A61K 31/4709* (2013.01); *A61K 31/407* (2013.01); *A61K 31/43* (2013.01); *A61K 31/4375* (2013.01); *A61K 31/496* (2013.01); *A61K 31/5377* (2013.01); *A61K 31/546* (2013.01); *A61K 31/65* (2013.01); *A61K 31/665* (2013.01); *A61K 31/675* (2013.01); *A61K 31/7036* (2013.01); *A61K 35/12* (2013.01); *A61K 38/12* (2013.01); *A61K 38/14* (2013.01); *A61K 45/06* (2013.01)

(58) Field of Classification Search
CPC .............. A61K 31/4709; A61K 31/665; A61K 31/496; A61K 31/43; A61K 31/546; A61K 31/407; A61K 31/5377; A61K 31/7036; A61K 31/65; A61K 38/12; A61K 38/14
See application file for complete search history.

(56) References Cited

FOREIGN PATENT DOCUMENTS

| WO | 02059116 A2 | 8/2002 | |
|---|---|---|---|
| WO | 03002560 A1 | 1/2003 | |
| WO | 03031443 A1 | 4/2003 | |
| WO | 03032962 A2 | 4/2003 | |
| WO | 2004/096221 A1 | 11/2004 | |
| WO | WO 2004096221 A1 * | 11/2004 | ......... A61K 31/4709 |
| WO | 2005023801 A1 | 3/2005 | |
| WO | 2005/058888 A2 | 6/2005 | |
| WO | 2007017828 A2 | 2/2007 | |
| WO | 2008056335 A1 | 5/2008 | |
| WO | 2008062379 A2 | 5/2008 | |
| WO | 2009/136379 A1 | 11/2009 | |

OTHER PUBLICATIONS

Moellering, R.C., "Rationale for Use of Antimicrobial Cominbinations," Am J Med. 75(2A): 4-8 (1983).
International Search Report issued in International Application No. PCT/EP2014/001450 dated Aug. 7, 2014.
Dowling et al., "The Clinical Use of Antibiotics in Combination", EdiItorials, A.M.A. Archives of Internal Medicine, 1957; 99(4): 536-538.
Leekha et al., "General Principles of Antimicrobial Therapy", Symposium on Antimicrobial Therapy, Feb. 2011; 86(2): 156-167.
Hubschwerlen et al., "Structure-Activity Relationship in the Oxazolidinone-Quinolone Hybrid Series: Influence of the Central Spacer on the Antibacterial Activity and the Mode of Action", Bioorganic & Medicinal Chemistry Letters 13 (2003) 4229-4233.
Hubschwerlen et al., "Design, Synthesis and Biological Evaluation of Oxazolidinone-Quinolone Hybrids" Bioorganic & Medicinal Chemistry 11 (2003) 2313-2319.
Dalhoff, et al., "Alternative Strategies for Proof-of-Principle Studies of Antibacterial Agents" Antimicrobial Agents and Chemotherapy, Aug. 2014, vol. 58, No. 8, pp. 4257-4263.
Rashid et al., "Ecological impact of MCB3837 on the normal human microbiota", International Journal of Antimicrobial Agents 2014, vol. 44, pp. 125-130.
Rashid et al., "In vitro activity of MCB36831 against Clostridium difficile strains", Anaerobe 2014, vol. 28, pp. 216-219.
Voigt et al., "Mode of action of MCB3681—analysis of MCB3681 proteome signature", pp. 1.

(Continued)

*Primary Examiner* — Kahsay Habte
(74) *Attorney, Agent, or Firm* — Mintz Levin Cohn Ferris Glovsky and Popeo, P.C.; Peter F. Corless

(57) ABSTRACT

The present invention provides a combination of at least one oxazolidinone-quinolone hybrid with at least one further antibacterial compound and the use thereof as drug, especially for the treatment or prophylaxis of bacterial infections.

14 Claims, No Drawings

(56) References Cited

OTHER PUBLICATIONS

M.T. Sweeney et al., "In Vitro Activities of Linezolid Combined with Other Animicrobial Agents against Staphylococci, Enterococci, Pneumococci, and Selected Gram-Negative Organisms", Antimicrobial Agents and Chemotherapy, 47(6), pp. 1902-1906 (Jun. 2003).

A. Dalhoff, "Quinolone-Oxazolidine Hybrids—Abstract", 47th Interscience Conference on Antimicrobial Agents and Chemotherapy (Sep. 17-20, 2007).

M.R. Barbachyn, "Recent Advances in the Discovery of Hybrid Antibacterial Agents", Annual Reports in Medicinal Chemistry, vol. 43, pp. 281-290 (2008).

* cited by examiner

COMBINATION THERAPY COMPRISING OXAZOLIDINONE-QUINOLONES FOR USE IN TREATING BACTERIAL INFECTIONS

RELATED APPLICATIONS

This application is a national stage application, filed under 35 U.S.C. § 371, of International Application No. PCT/EP2014/001450, filed on May 28, 2014, and claims priority to European Patent Application No. 13002761.8, filed on May 28, 2013, both of which, including their contents, are incorporated herein by reference in their entireties.

The present invention provides a combination of at least one oxazolidinone-quinolone hybrid molecule with at least one further antibacterial compound and the use thereof as a drug, especially for the treatment or prophylaxis of bacterial infections.

Combinations of antimicrobials have long been used to provide antibacterial activity against multiple potential pathogens for initial empirical treatment of critically ill patients. The rationale for combining two or more antibacterial agents is threefold:

1. Antibacterials are combined either to complement their spectra or to enhance the activity of either antibacterial agent by achievement of a synergistic effect. Synergy is defined as the combined effect of two or more antibacterial agents, which is significantly greater than that provided by the sum of each antibacterial agent alone. However, additive, indifferent or antagonistic effects may result from antibacterial drug-combinations, too.

2. The doses of either antibacterial can be lowered in order to reduce their toxicity.

3. The use of two or more antibacterials might prevent or reduce the emergence of resistance to either antibacterial agent (Dowling H. F., Finland M., Hamburger M., Jawetz E., Knight V., Lepper M H. H., Meiklejohn G., Rantz L. A., Rhoads P. S. The clinical use of antibiotics in combination. AMA Arch Intern Med 1957; 99 (4): 536-538; Moellering R. C. Rationale for use of antimicrobial combinations. Ann J Med 1983; 75 (2A): 4-8). In an era of increasing drug resistance, and in particular, multidrug resistance, the use of antibacterial drug combinations has evolved. Under these circumstances, the achievement of synergy is no longer the only required result of combination therapy, because any clinical activity of an antibacterial drug combination can be advantageous over the inactivity of each drug alone. Thus, an acceptable effect may result from additive or even indifferent activity of the combination. An acceptable result may also derive from the improved performance of a single active antibacterial agent, in particular in case it is not so well tolerated, by an otherwise inactive agent. In this case, prevention of resistance to the active antibacterial agent may be possible.

Because microbiological results of susceptibility testing usually only become available after 24 to 72 hours, initial therapy of infection is most frequently empiric and guided by the clinical presentation. It has been shown that inadequate initial therapy of infections in critically ill, hospitalized patients is associated with poor outcomes, including greater morbidity and mortality as well as increased length of stay. Therefore, a common approach in initial empiric antibacterial therapy—in particular in therapy of difficult to treat pathogens—is to use a combination of antimicrobial agents in order to extend the antibacterial spectrum. This is true for both community- and hospital-acquired infections (Leekha S., Terrell C. L., Edson R. S. General Principles of Antimicrobial Therapy; Mayo Clin Proc. 2011; 86 (2): 156-167).

Oxazolidinone-quinolone hybrids are compounds in which the pharmacophores of quinolones and oxazolidinones are linked together through a linker that is stable under physiological conditions. These compounds are useful antimicrobial agents.

Oxazolidinone-quinolone hybrid antibacterials and methods for their preparation are e.g. described in WO02059116, WO03002560, WO03031443, WO03032962, WO2005058888, WO2005023801, WO2004096221, WO2007017828, WO2008056335, WO2008062379 and WO2009136379.

It has now been found that a combination of an oxazolidinone-quinolone hybrid antibacterial with at least one further antibacterial compound leads to an unexpected improvement in the antibacterial spectrum and/or antibacterial activity of the corresponding pharmaceutical compositions.

The present invention provides a combination of:

i) at least one (preferably one) oxazolidinone-quinolone hybrid with ii) at least one (preferably one) further antibacterial compound which is different from compound (i).

The present invention further provides a pharmaceutical composition comprising:

i) at least one (preferably one) oxazolidinone-quinolone hybrid and ii) at least one (preferably one) further antibacterial compound which is different from compound (i).

The present invention moreover provides a kit-of-parts comprising:

i) at least one (preferably one) oxazolidinone-quinolone hybrid and ii) at least one (preferably one) further antibacterial compound which is different from compound (i).

The combinations (e.g. the pharmaceutical compositions and/or kit-of-parts) of the present inventions may be used in the treatment and/or prophylaxis of bacterial infections.

Preferably, the at least one oxazolidinone-quinolone hybrid is selected from the compounds described in WO02059116, WO03002560, WO03031443, WO03032962, WO2005058888, WO2005023801, WO2004096221, WO2007017828, WO2008056335, WO2008062379 and/or WO2009136379.

More preferred oxazolidinone-quinolone hybrids are compounds of formula (I),

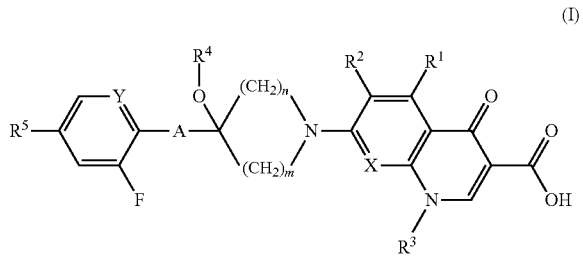

wherein
A is an alkylene group, an alkenylene group, an alkynylene group, a heteroalkylene group, a cycloalkylene group, a heterocycloalkylene group, an alkylcycloalkylene group, a heteroalkylcycloalkylene group, an arylene group or a heteroarylene group all of which groups may be substituted;
X is $CR^7$ or N;
Y is $CR^6$ or N;
n is 1, 2 or 3;
m is 1, 2 or 3;
$R^1$ is H, F, Cl, Br, I, OH, $NH_2$, an alkyl group or a heteroalkyl group;
$R^2$ is H, F or Cl;
$R^3$ is H, an alkyl group, an alkenyl group, an alkynyl group, a heteroalkyl group, a cycloalkyl group, a heterocycloalkyl group, an alkylcycloalkyl group, a heteroalkylcycloalkyl group, an aryl group, a heteroaryl group, an aralkyl group or a heteroaralkyl group; all of which groups may be substituted with one, two or more halogen atoms like F or Cl or amino groups;
$R^4$ is hydrogen, a group of formula $PO_3R^9{}_2$ or $SO_3R^{10}$ or a heteroalkyl group carrying at least one OH, $NH_2$, $SO_3R^{10}$, $PO_3R^9{}_2$ or COOH group or an ester of a naturally occurring amino acid or a derivative thereof, wherein the groups $R^9$ independently of each other are H, alkyl, cycloalkyl, aryl or aralkyl and wherein $R^{10}$ is H, alkyl, cycloalkyl, aryl or aralkyl;
$R^5$ is selected from following groups:

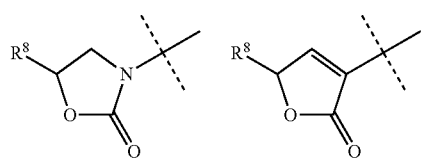

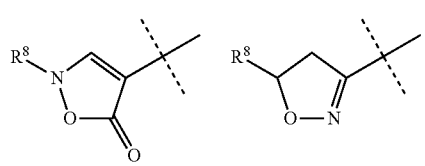

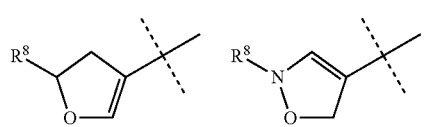

$R^6$ is H, F, Cl or OMe;
$R^7$ is H, F, Cl, OH, $NH_2$, a substituted or unsubstituted alkyl group or a substituted or unsubstituted heteroalkyl group, or $R^3$ and $R^7$ can be linked via an alkylene, an alkenylene or a heteroalkylene group or be a part of a cycloalkylene or heterocycloalkylene group; in case $R^3$ is no H and $R^7$ is no H, F, OH, $NH_2$ or Cl; and
$R^8$ is a $C_{1-6}$ alkyl, a $C_{1-6}$ heteroalkyl or a heteroaralkyl group; or a pharmacologically acceptable salt, solvate or hydrate thereof.

The term alkyl refers to a saturated straight or branched chain hydrocarbon group, preferably containing from one to ten, preferably one to six carbon atoms, for example methyl, ethyl, propyl, isopropyl, butyl, iso-butyl, sec-butyl, tert-butyl, n-pentyl, iso-pentyl, n-hexyl, 2,2-dimethylbutyl, n-octyl or n-pentyl groups. Any alkyl group as defined herein may be substituted with one, two or more substituents, for example F, Cl, Br, I, $NH_2$, OH, SH or $NO_2$.

The terms alkenyl and alkynyl refer to an unsaturated straight or branched chain hydrocarbon group (having one, two or more double and/or triple bonds, an alkenyl preferably having one or two double bonds and an alkynyl preferably having one or two triple bonds), preferably containing two to ten, preferably two to six carbon atoms for example: ethenyl (vinyl), propenyl (allyl), iso-propenyl, n-pentenyl, butenyl, isoprenyl or hexa-2-enyl; ethynyl, propynyl or butynyl groups. Any alkenyl or alkynyl group as defined herein may be substituted with one, two or more substituents, for example F, Cl, Br, I, $NH_2$, OH, SH or $NO_2$.

The term heteroalkyl refers to an alkyl, alkenyl or alkynyl group as defined herein where one or more carbon atoms are replaced by an oxygen, nitrogen, phosphorous or sulphur atom, for example an alkoxy group such as methoxy, ethoxy, propoxy, iso-propoxy, butoxy or tert.-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. The term heteroalkyl furthermore refers to a group derived from a carboxylic acid or carboxylic acid amide such as acetyl, propionyl, acetyloxy, propionyloxy, acetylamino or propionylamino, a carboxyalkyl group such as carboxymethyl, carboxyethyl or carboxypropyl, a carboxyalkyl ester, an alkylthiocarboxyamino group, an alkoxyimino group, an alkylaminothiocarboxyamino group or an alkoxycarbonylamino group. Any heteroalkyl group as defined herein may be substituted with one, two or more substituents, for example F, Cl, Br, I, $NH_2$, OH, SH or $NO_2$.

The term cycloalkyl refers to a saturated or partially unsaturated (having one, two or more double and/or triple bonds) cyclic group with one, two or more rings, having three to 14 carbon ring-atoms, preferably from five or six to ten carbon ring-atoms, for example cyclopropyl, cyclobutyl, cyclopentyl, cyclohexyl, tetralin, cyclopentenyl or cyclohex-2-enyl groups. Any cycloalkyl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide.

The term heterocycloalkyl refers to a cycloalkyl group as defined herein where one, two or more carbon ring-atoms are replaced by one, two or more oxygen, nitrogen, phosphorous or sulphur atoms or $S(O)_{1-2}$ groups for example piperidino, morpholino or piperazino groups.

The term alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The term heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom). A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The term aryl refers to an aromatic cyclic group with one, two or more rings, having five to 14 carbon ring-atoms preferably from five or six to ten carbon ring-atoms, for example phenyl or naphthyl groups. Any aryl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide.

The term heteroaryl refers to an aryl group as defined herein where one, two or more ring-carbon atoms are replaced by an oxygen, nitrogen, boron, phosphorous or sulphur atom, for example pyridyl, imidazolyl, pyrazolyl, quinolinyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl and pyridazinyl groups.

The term aralkyl (or arylalkyl or alkylaryl) refers to groups that comprise both aryl as well as alkyl, alkeny, alkynyl and/or cycloalkyl groups.

The term heteroaralkyl (or heteroarylalkyl or heteroalkylaryl or heteroalkylheteroaryl) refers to an aralkyl group as defined herein where one, two, three or more carbon atoms are replaced by one, two, three or more oxygen, nitrogen, phosphorous or sulphur atoms or $S(O)_{1-2}$ groups.

The expression "optionally substituted" especially refers to groups in which one, two, three or more hydrogen atoms may have been replaced by fluorine, chlorine, bromine or iodine atoms or by OH, =O, SH, =S, $NH_2$, =NH, $N_3$ or $NO_2$ groups. This expression refers furthermore to groups that may be substituted by one, two, three or more unsubstituted $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

In the context of the present invention, the terms antibacterial agent(s), antibacterial(s), antimicrobial(s), antimicrobial agent(s) and antibacterial compound(s) preferably have the same meaning.

Preferred are compounds of Formula (I), wherein $R^1$ is H.

Further preferred are compounds of Formula (I), wherein $R^2$ is F or H; especially preferably, $R^2$ is F.

Moreover preferred are compounds of Formula (I), wherein $R^3$ is an ethyl, a 2-propyl, a $C_3$-$C_6$ cycloalkyl (i.e. cyclopropyl, cyclobutyl, cyclopentyl or cyclohexyl), a phenyl or a pyridyl group. All these groups may be substituted with one, two, three or more fluorine atoms or amino groups.

Moreover preferred are compounds of Formula (I), wherein $R^3$ is a cyclopropyl group.

Further preferred are compounds of Formula (I), wherein $R^7$ and $R^3$ together form a bridge of the formula —O—$CH_2$—N(Me)- or —O—$CH_2$—CH(Me)- (especially —O—$CH_2$—CH(Me)-). Herein, the preferred stereochemistry at the chiral center is the one giving the (S) configuration in the final compound.

Moreover preferred are compounds of formula (I), wherein $R^4$ is hydrogen or a group of formula $SO_3H$, $PO_3H_2$, $CH_2OPO_3H_2$ or $COCH_2CH_2COOH$.

Further preferred are compounds of formula (I), wherein $R^4$ is an ester of a naturally occurring amino acid or a derivative thereof (e.g. a group of formula —COCHR'$NH_2$ or a derivative like an ester, amide or alkylamine thereof, wherein R' is the side chain of a naturally occurring amino acid like aspartic acid, glutaric acid, lysine, etc; e.g. dimethyl aminoglycine $COCH_2N(CH_3)_2$).

Especially preferred are compounds of formula (I), wherein $R^4$ is hydrogen or a group of formula $PO_3H_2$.

Moreover preferred are compounds of Formula (I), wherein $R^5$ has the following structure:

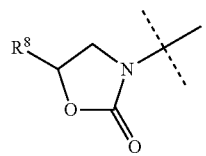

Especially preferred are compounds of Formula (I), wherein R⁵ has the following structure:

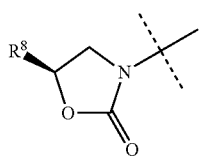

Further preferred are compounds of Formula (I), wherein R⁸ is a $C_{1-6}$ alkyl or a $C_{1-6}$ heteroalkyl group.

Moreover preferred are compounds of Formula (I), wherein R⁸ is a group of the formula —CH₂NHCOCH=CHAryl, —CH₂OHeteroaryl (especially-oxa-3-oxazol), —CH₂NHSO₂Me, —CH₂NHCOOMe, —CH₂NHCOMe, —CH₂OH, —CH₂NHCS₂Me, —CH₂NHCSMe, —CH₂NHCSNH₂, —CH₂NHCSOMe or —NHCOMe; especially —CH₂OH or —CH₂NHCOMe.

Especially preferred are compounds of Formula (I), wherein R⁵ has the following structure:

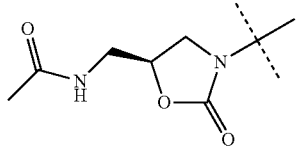

Moreover preferred are compounds of Formula (I), wherein R⁷ is H, F, Cl or a methoxy group that may be substituted by one, two or three fluorine atoms.

Especially preferred are compounds of Formula (I), wherein R⁷ is H or a methoxy group.

Further preferred are compounds of formula (I), wherein X is N or CH; especially preferably, X is CH.

Moreover preferred are compounds of Formula (I), wherein Y is CH.

Further preferred are compounds of Formula (I), wherein n is 1 or 2.

Further preferred are compounds of Formula (I), wherein m is 2.

Especially preferred are compounds of Formula (I), wherein n is 2 and m is 2.

Further preferred are compounds of Formula (I), wherein A is $C_{1-6}$ alkylene, $C_{2-6}$ alkenylene, $C_{2-6}$ alkynylene, $C_{1-6}$ heteroalkylene, cyclopropylene, epoxide, aziridine, thioepoxide, lactame or lactone, all of which groups may be substituted.

Moreover preferred are compounds of formula (I), wherein A is a group of Formula —O—B—, wherein the oxygen is bound to the phenyl or pyridyl group and wherein B is a $C_{1-4}$ alkylene group, a $C_{2-4}$ alkenylene group, a $C_{2-4}$ alkynylene group or a $C_{1-4}$ heteroalkylene group, all of which groups may be substituted by one, two or more hydroxy or amino groups.

Especially preferred are compounds of formula (I), wherein A is a group of formula —CH₂CH₂—, —OCH₂—, —OCH₂CH₂—, —SCH₂—, —SCH₂CH₂—, —CH=CH—, —C≡C—, —CH(OH)CH(OH)— or —CH(NH₂)CH(OH)—.

Especially preferred are compounds of formula (I), wherein B is CH₂ or CH₂CH₂.

Especially preferred oxazolidinone-quinolone hybrids are compounds of formula (II)

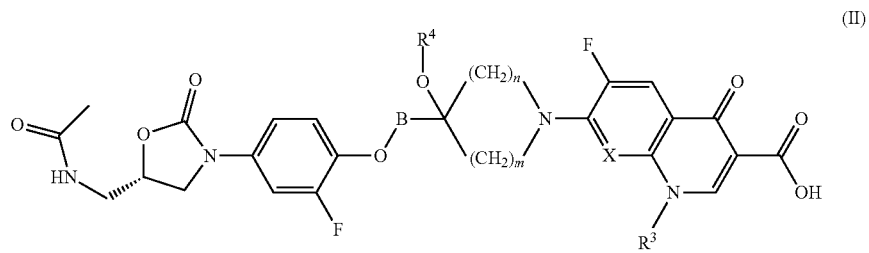

wherein the residues are defined as above, or a pharmacologically acceptable salt, solvate or hydrate thereof. In a preferred embodiment B is $CH_2$ or $CH_2CH_2$; X is CH, N or C—OMe and $R^3$ is cyclopropyl or X is $CR^7$ and $R^7$ and $R^3$ together form a bridge of the formula —O—$CH_2$—CH(Me)-, wherein the preferred stereochemistry at the chiral center is the one giving the (S) configuration in the final compound, n is 1, 2 or 3 (preferably 2), m is 2 and $R^4$ is hydrogen or a group of formula $PO_3H_2$.

Moreover preferred are the mono, di or tri sodium salts (most preferred the mono sodium salts) of compounds of formula (I) or (II) or mixtures thereof. Especially preferred are the mono, di or tri sodium salts (most preferred the mono sodium salts) of compounds of formula (I) or (II), wherein $R^4$ is $PO_3H_2$ or mixtures thereof.

Especially preferred is the mono sodium salt of a compound of formula (II) wherein $R^3$ is a cyclopropyl group, X is CH or N, n is 2, m is 2, $R^4$ is $PO_3H_2$ and B is $CH_2$.

It should be appreciated that certain compounds of formula (I) or (II) as mentioned in this description may have tautomeric forms from which only one might be specifically mentioned or depicted in this description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). Further, some compounds may display polymorphism. All these tautomeric forms, geometrical or optical isomers (as well as racemates and diastereomers) and polymorphous forms are included in the invention.

Specific preferred examples of compounds of formula (I) and/or (II) are:

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic acid:

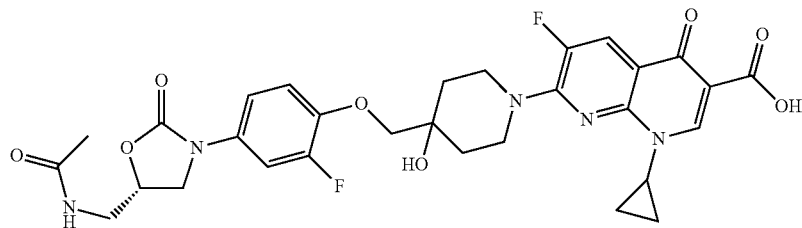 [SMILES: CC(=O)NC[C@H]1CN(c2ccc(OCC3(O)CCN(c4nc5c(cc4F)c(=O)c(C(=O)O)cn5C4CC4)CC3)c(F)c2)C(=O)O1]

7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-[1,8]naphthyridine-3-carboxylic acid:

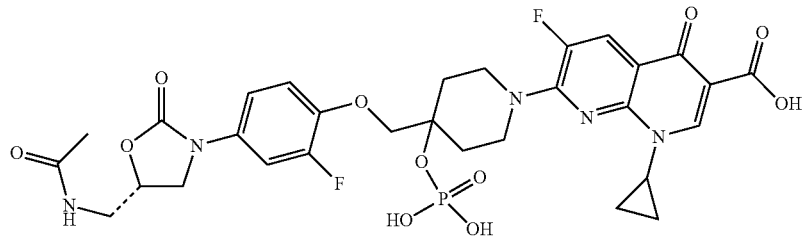 [SMILES: CC(=O)NC[C@H]1CN(c2ccc(OCC3(OP(=O)(O)O)CCN(c4nc5c(cc4F)c(=O)c(C(=O)O)cn5C4CC4)CC3)c(F)c2)C(=O)O1]

11

7-[4-{4-[(5S)-5-(acetylamino-methyl)-2-oxo-oxazolidin-3-yl]-2-fluoro-phenoxymethyl}-4-(2,6-diamino-hexanoyloxy)-piperidin-1-yl]-1-cyclopropyl-6-fluoro-4-oxo-1,4-dihydro-[1,8]naphthyridine-3-carboxylic acid:

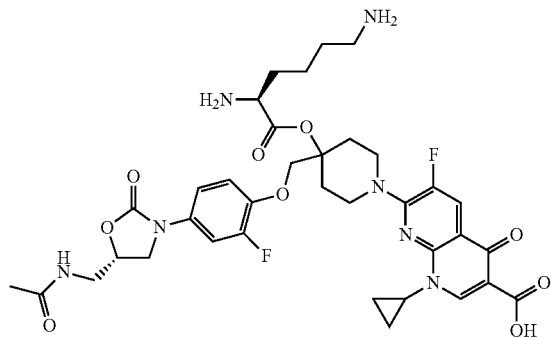 [SMILES: CC(=O)NC[C@H]1CN(c2ccc(OCC3(OC(=O)[C@@H](N)CCCCN)CCN(c4nc5c(cc4F)c(=O)c(C(=O)O)cn5C4CC4)CC3)c(F)c2)C(=O)O1]

Succinic acid mono-[4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl] ester:

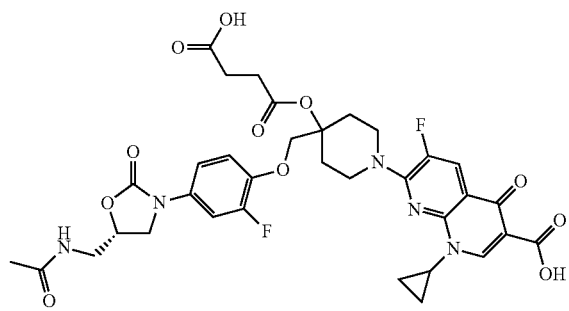 [SMILES: CC(=O)NC[C@H]1CN(c2ccc(OCC3(OC(=O)CCC(=O)O)CCN(c4nc5c(cc4F)c(=O)c(C(=O)O)cn5C4CC4)CC3)c(F)c2)C(=O)O1]

12

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

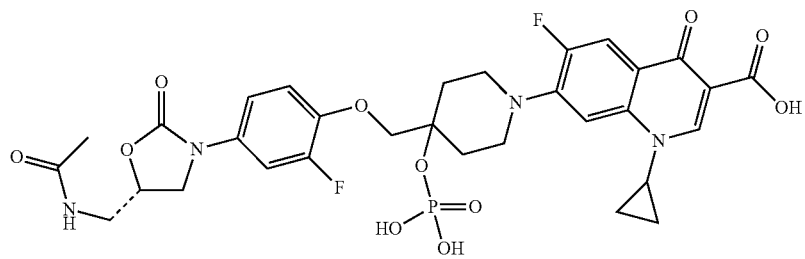 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-8-methoxy-4-oxo-1,4-dihydro-quinoline-3-carboxylic acid:

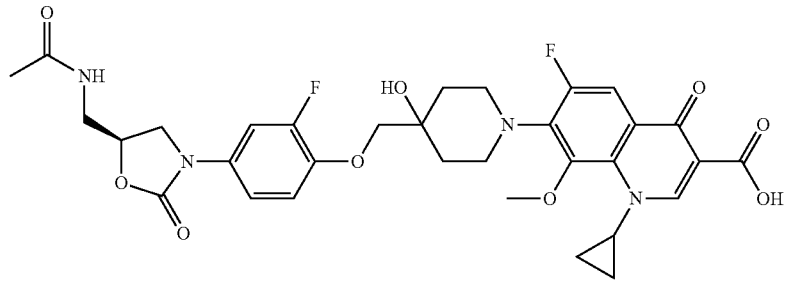 [SMILES: COc1c(N2CCC(O)(COc3ccc(N4C[C@H](CNC(C)=O)OC4=O)cc3F)CC2)c(F)cc2c(=O)c(C(=O)O)cn(C3CC3)c12]

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-8-methoxy-4-oxo-1,4-dihydro-quinoline-3-carboxylic acid:

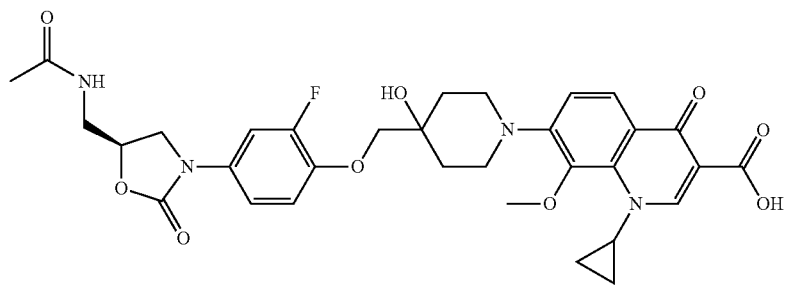 [SMILES: COc1c(N2CCC(O)(COc3ccc(N4C[C@H](CNC(C)=O)OC4=O)cc3F)CC2)ccc2c(=O)c(C(=O)O)cn(C3CC3)c12]

9-(4-{4-[(5S)-5-(acetylamino-methyl)-2-oxo-oxazolidin-3-yl]-2-fluoro-phenoxymethyl}-4-hydroxy-piperidin-1-yl)-8-fluoro-3-methyl-6-oxo-2,3-dihydro-6H-1-oxa-3a-aza-phenalene-5-carboxylic acid:

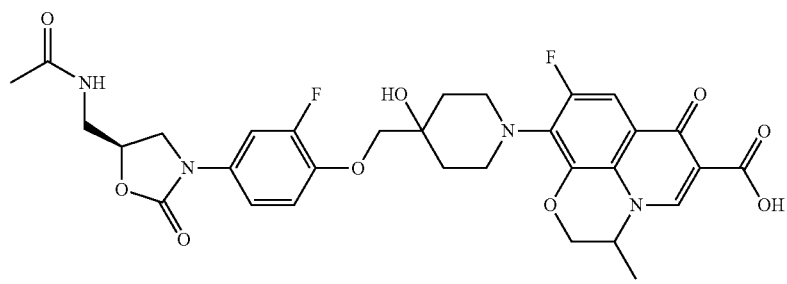 [SMILES: CC(=O)NC[C@H]1CN(c2ccc(OCC3(O)CCN(c4c(F)cc5c(=O)c(C(=O)O)cn6c5c4OCC6C)CC3)c(F)c2)C(=O)O1]

7-(3-{4-[(5S)-5-(acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-[1,8]naphthyridine-3-carboxylic acid:

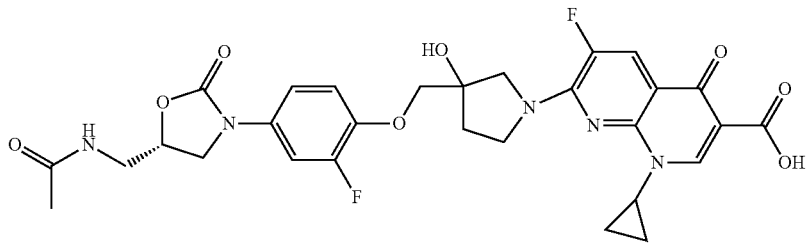 [SMILES: CC(=O)NC[C@H]1CN(c2ccc(OCC3(O)CCN(c4nc5c(cc4F)c(=O)c(C(=O)O)cn5C4CC4)C3)c(F)c2)C(=O)O1]

7-(3-{4-[(5S)-5-(acetylamino-methyl)-2-oxo-oxazolidin-3-yl]-2-fluoro-phenoxymethyl}-3-hydroxy-pyrrolidin-1-yl)-1-cycloprapyl-6-fluoro-4-oxo-1,4-dihydro-quinoline-3-carboxylic acid:

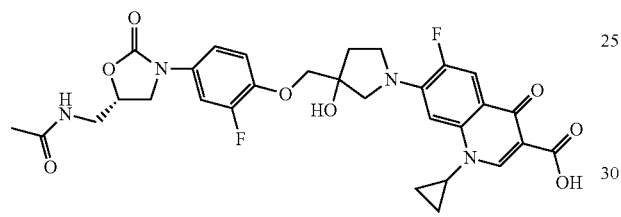

7-(3-{4-[(5S)-5-(acetylamino-methyl)-2-oxo-oxazolidin-3-yl]-2-fluoro-phenoxymethyl}-3-hydroxy-pyrrolidin-1-yl)-1-cyclopropyl-6-fluoro-8-methoxy-4-oxo-1,4-dihydro-quinoline-3-carboxylic acid:

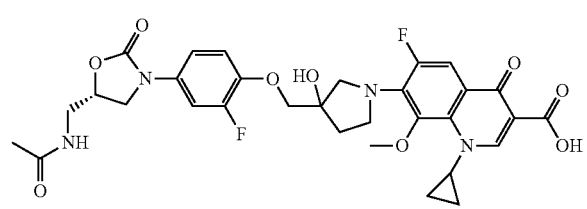 [SMILES: COc1c(N2CCC(O)(COc3ccc(N4C[C@H](CNC(C)=O)OC4=O)cc3F)C2)ccc2c(=O)c(C(=O)O)cn(C3CC3)c12]

7-(3-{4-[(5S)-5-(acetylamino-methyl)-2-oxo-oxazolidin-3-yl]-2-fluoro-phenoxymethyl}-3-hydroxy-pyrrolidin-1-yl)-1-cyclopropyl-8-methoxy-4-oxo-1,4-dihydro-quinoline-3-carboxylic acid:

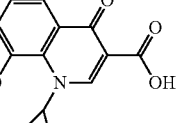

9-(3-{4-[(5S)-5-(acetylamino-methyl)-2-oxo-oxazolidin-3-yl]-2-fluoro-phenoxymethyl}-3-hydroxy-pyrrolidin-1-yl)-8-fluoro-3-methyl-6-oxo-2,3-dihydro-6H-1-oxa-3a-aza-phenalene-5-carboxylic acid:

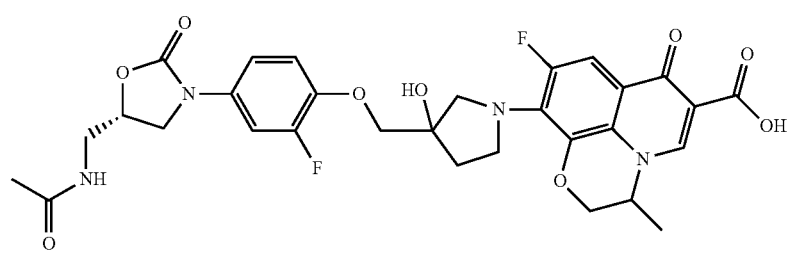 [SMILES: CC(=O)NC[C@H]1CN(c2ccc(OCC3(O)CCN(c4c(F)cc5c(=O)c(C(=O)O)cn6c5c4OCC6C)C3)c(F)c2)C(=O)O1]

7-(4-{4-[(5S)-5-(acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-quinoline-3-carboxylic acid:

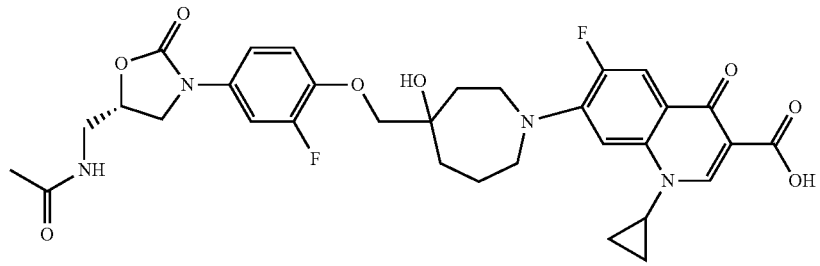 [SMILES: CC(=O)NC[C@H]1CN(c2ccc(OCC3(O)CCCN(c4cc5c(cc4F)c(=O)c(C(=O)O)cn5C4CC4)CC3)c(F)c2)C(=O)O1]

7-(4-{4-[(5S)-5-(acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-[1,8]naphthyridine-3-carboxylic acid:

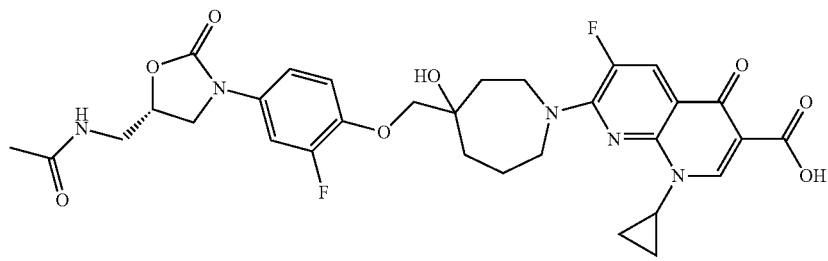 [SMILES: CC(=O)NC[C@H]1CN(c2ccc(OCC3(O)CCCN(c4nc5c(cc4F)c(=O)c(C(=O)O)cn5C4CC4)CC3)c(F)c2)C(=O)O1]

sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid;

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-quinoline-3-carboxylic acid:

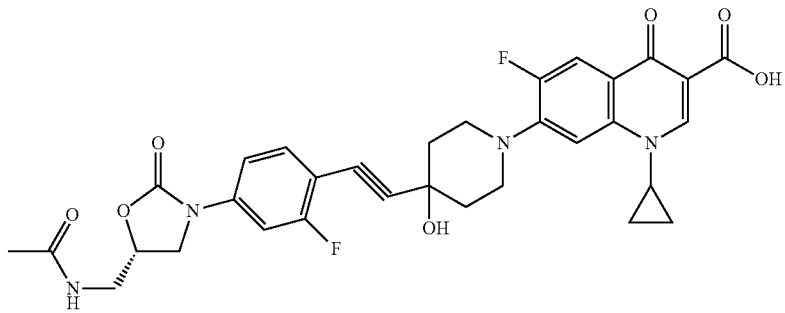 [SMILES: CC(=O)NC[C@H]1CN(c2ccc(C#CC3(O)CCN(c4cc5c(cc4F)c(=O)c(C(=O)O)cn5C4CC4)CC3)c(F)c2)C(=O)O1]

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-[1,8]-napthyridine-3-carboxylic acid:

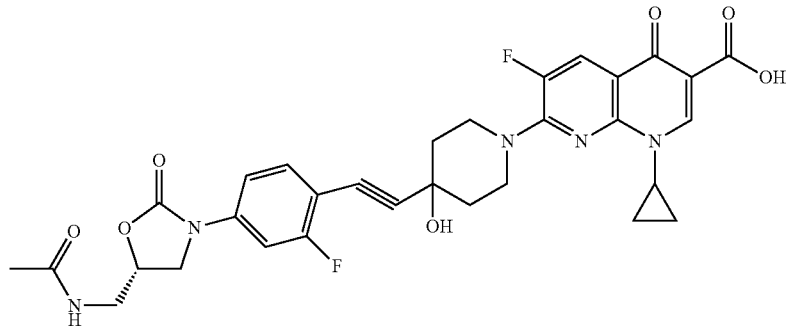 [SMILES: CC(=O)NC[C@H]1CN(c2ccc(C#CC3(O)CCN(c4nc5c(cc4F)c(=O)c(C(=O)O)cn5C4CC4)CC3)c(F)c2)C(=O)O1]

7-[4-(2-{4-[5S-(acetylamino-methyl)-2-oxo-oxazolidin-3-yl]-2-fluoro-phenyl}-ethyl)-4-hydroxy-piperidin-1-yl]-1-cyclopropyl-6-fluoro-4-oxo-1,4-dihydro-quinoline-3-carboxylic acid:

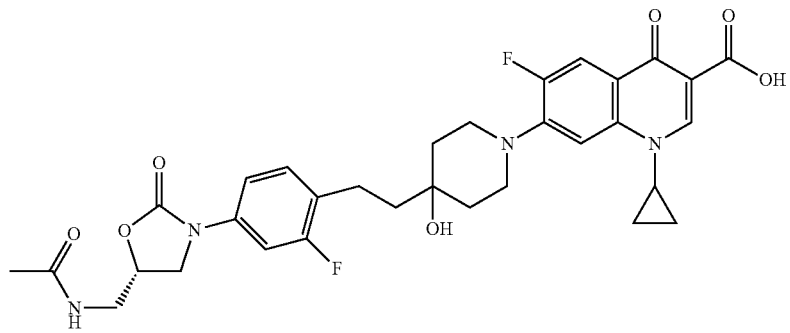 [SMILES: CC(=O)NC[C@H]1CN(c2ccc(CCC3(O)CCN(c4cc5c(cc4F)c(=O)c(C(=O)O)cn5C4CC4)CC3)c(F)c2)C(=O)O1]

and 1-cyclopropyl-6-fluoro-7-[4-({2-fluoro-4-[(5R)-5-(hydroxymethyl)-2-oxo-1,3-oxazolidin-3-yl]phenoxy}methyl)-4-hydroxypiperidin-1-yl]-4-oxo-1,4-dihydroquinolin-3-carboxylic acid:

or a pharmacologically acceptable salt, solvate or hydrate thereof.

Especially preferably, the at least one oxazolidinone-quinolone hybrid is selected from the following compounds:

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

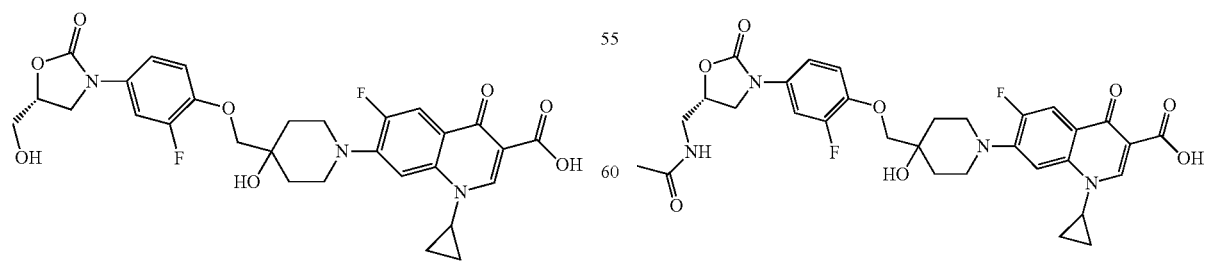

and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

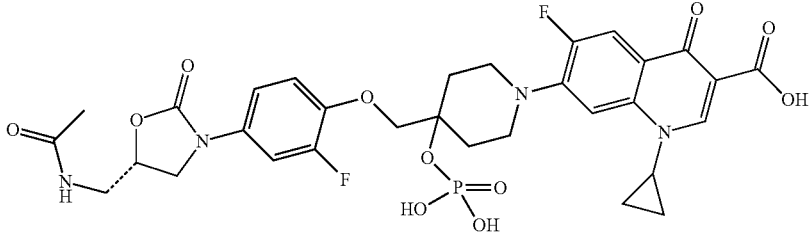 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid and salts thereof are prodrugs of active drug 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid.

When intravenously administered to several animal species, among them mice and rats, the sodium salt of 7-(4-{4-[(5S)-5-(Acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid (Compound 1) was rapidly converted to the active substance 7-(4-{4-[(5S)-5-(Acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid (Compound 2). The very good solubility in aqueous media allows for (Compound 1) to be easily formulated, using lyophilisation. To improve stability and to reduce reconstitution time of the lyophilisate, Compound 1 can e.g. be formulated together with sorbitol and sodium hydroxide and lyophilised in glass vials. The lyophilisate can be easily reconstituted by addition of water for injection and gentle shaking to form a yellow, sterile solution ready for intravenous injection.

Preferably, the at least one further antibacterial compound (ii) is selected from the following compounds:
β-lactams:
  penems including carba-, thio-, and oxapenems such as imipenem, meropenem, ertapenem, biapenem, faropenem;
  cephalosporines such as cefazolin, cefepime, cefotaxime, cefoxitine, ceftaroline, ceftazidime, ceftobiprole, ceftriaxone, cefuroxime and cephalexine;
  monobactames such as aztreonam, BAL30072;
  penicillines such as penicillin G (benzylpenicillin), penicillin V (phenoxymethylpenicillin); acylaminopenicillines such as piperacillin, mezlocillin, azlocillin; aminopenicillines such as ampicillin, amoxicillin; isoxazolylpenicillines such as oxacillin, cloxacillin, dicloxacillin, flucloxacillin; methicillin; sultamicillin; ticarcillin, carbenicillin, temocillin;
  combinations of β-lactams with a β-lactamase inhibitor such as clavulanic acid+amoxicillin, sulbactam+ampicillin, tazobactam+piperacillin, ticarcillin+clavulanate, ceftazidime+avibactam, ceftaroline+avibactam, imipenem+MX-7655, biapenem+RPX7009, aztreonam+avibactam;
fosfomycin;
fosmidomycin;
glycopeptides such as teicoplanin, vancomycin;
lipopeptides such as daptomycin;
lipoglycopeptides such as telavancin, oritavancin, dalbavancin;
other agents active against Gram-positive bacteria such as GSK-1322322, AFN-1252, MUT-056399;
polypeptides such as bacitracin, colistin, gramicidin, polymyxin B, tyrothricin;
other membrane-acting agents such as brilicidin, POL7080, ACHN-975;
aminoglykosides such as amikacin, gentamicin, kanamycin, neomycin, netilmicin, streptomycin, tobramycin;
chloramphenicol, thiamphenicol;
fusidic acid;
macrolides such as azithromycin, clarithromycin, erythromycin, roxythromycin,
ketolides such as cethromycin, narbomycin, telithromycin, solithromycin;
lincosamides such as clindamycin, lincomycin;
Streptogramines such as dalfopristin, quinupristin;
polyketides
oxazolidinones such as linezolid, tedizolid, radezolid;
tetracyclines such as doxycyclin, minocyclin, tetracyclin, oxytetracyclin;
glycylcyclines such as tigecyclin, omadacycline;
type II topopisomerase inhibitors:
  quinolones (especially fluoroquinolones) such as norfloxacin, enoxacin, ciprofloxacin, ofloxacin, levofloxacin, gatifloxacin, grepafloxacin, moxifloxacin, delafloxacin, finafloxacin, nemonoxacin, zabofloxacin, ozenoxacin, chinfloxacin, JNJ-Q2, DS-8587, KPI-10, GSK2140944, ACH-702;
  coumarins such as novobiocin, clorobiocin, coumermycin A;
nitroimidazoles such as metronidazole, tinidazole, ornidazole, nimorazole;

folic acid agonists:
   sulfonamides such as sulfadiazin, sulfadoxin, sulfamethoxazole, sulfasalazin;
   diaminopyrimidines such as pyrimethamin, trimethoprim;
ansamycines:
   rifamycines such as rifampicin, rifabutin, rifapentin, rifamixin;
additional classes:
   pleuromutilines such as BC-3781, BC-7013;
   leucyl-t-RNA synthase inhibitors such as AN3365.

More preferably, the at least one further antibacterial compound (ii) is selected from the following compounds: colistin, fosfomycin, tobramycin, ciprofloxacin, tigecycline, imipenem, piperacillin-tazobactam, ceftazidime, ampicillin, ceftriaxone, vancomycin, daptomycin, moxifloxacin and linezolid.

Especially preferably, the at least one further antibacterial compound (ii) is selected from the following compounds: colistin, fosfomycin, ampicillin, ceftriaxone, moxifloxacin and linezolid.

According to an especially preferred embodiment, the present invention provides a combination and/or a pharmaceutical composition and/or a kit-of-parts comprising:
i) an oxazolidinone-quinolone hybrid and
ii) a further antibacterial compound which is different from compound (i), wherein the oxazolidinone-quinolone hybrid is selected from the following compounds:
7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

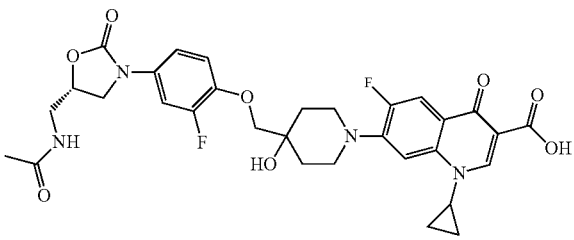 [SMILES: CC(=O)NC[C@H]1CN(c2ccc(OCC3(O)CCN(c4cc5c(cc4F)c(=O)c(C(=O)O)cn5C4CC4)CC3)c(F)c2)C(=O)O1]

and
7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

or a salt, solvate or hydrate thereof (such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid); and
wherein the further antibacterial compound (ii) is selected from the following compounds: colistin, fosfomycin, ampicillin, ceftriaxone, moxifloxacin and linezolid.

According to a further preferred embodiment, the at least one further antibacterial compound (ii) is selected from the following compounds: colistin and other polycations (or polycationic antibacterials) such as bacitracin, gramicidin, polymyxin B, tyrothricin, and aminoglycosides (e.g. amikacin, gentamicin, kanamycin, neomycin, netilmicin, streptomycin and tobramycin).

Especially preferably, the further antibacterial compound (ii) is colistin.

If colistin or other polycations (or polycationic antibacterials) such as bacitracin, gramicidin, polymyxin B, tyrothricin, and aminoglycosides (e.g. amikacin, gentamicin, kanamycin, neomycin, netilmicin, streptomycin and tobramycin) (especially colistin) are used as further antibacterial compound (ii), it is preferred that the corresponding pharmaceutical compositions and/or the combinations of the present invention are applied topically, e.g. to the eye, ear, respiratory tract, skin and soft tissue, urethra and urinary bladder, oral cavity, abdominal cavity or pleural cavity, or any surgical site. They can in particular be used for the treatment or prophylaxis of bacterial infections caused by Gram-negative bacteria such as Enterobacteriaceae and non-fermenters including but not limited to ESBL- and/or AmpC producing isolates as well as by Gram-positive bacteria including but not limited to multi-drug- and/or methicillin-resistant staphylococci (e.g. MRSA or MRSE), multi-drug- and/or penicillin-resistant streptococci (e.g. PRSP), and multi-drug- and/or vancomycin-resistant enterococci (e.g. VRE).

If colistin or other polycations (or polycationic antibacterials) such as bacitracin, gramicidin, polymyxin B, tyrothricin and aminoglycosides (e.g. amikacin, gentamicin, kanamycin, neomycin, netilmicin, streptomycin and tobramycin) (especially colistin) are used as further antibacterial compound (ii), it is furthermore preferred that the corresponding pharmaceutical compositions and/or the combinations of the present invention are applied parenterally. They can in particular be used for the treatment or prophylaxis of bacterial infections caused by Gram-negative bacteria such as Enterobacteriaceae and non-fermenters includ-

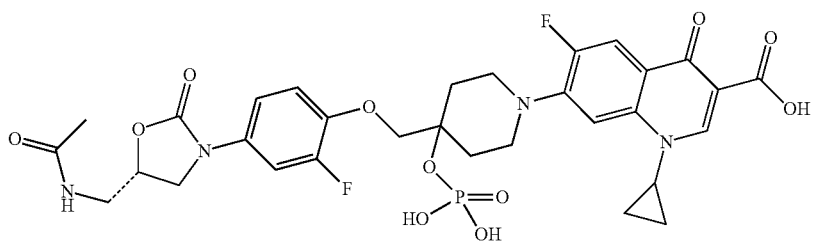 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

ing but not limited to ESBL- and/or AmpC producing isolates as well as Gram-positive bacteria including but not limited to multi-drug- and/or methicillin-resistant staphylococci (e.g. MRSA or MRSE), multi-drug- and/or penicillin-resistant streptococci (e.g. PRSP), and multi-drug- and/or vancomycin-resistant enterococci (e.g. VRE). Such infections include cardiovascular, central nervous system, circulatory, gastrointestinal, genitourinary, intra-abdominal, lower/upper respiratory, skeletal (bones and joints), and skin and soft tissue infections including diabetic foot.

According to a further preferred embodiment, the at least one further antibacterial compound (ii) is selected from the following compounds: fluoroquinolones such as norfloxacin, enoxacin, ciprofloxacin, ofloxacin, levofloxacin, gatifloxacin, grepafloxacin, moxifloxacin, delafloxacin, nemonoxacin, zabofloxacin, ozenoxacin, chinfloxacin, JNJ-Q2, DS-8587, KPI-10, GSK2140944, ACH-702 and finafloxacin, as well as oxazolidinones such as linezolid, tedizolid and radezolid.

Further especially preferably, the at least one further antibacterial compound (ii) is selected from the following compounds: linezolid and moxifloxacin.

If fluoroquinolones such as norfloxacin, enoxacin, ciprofloxacin, ofloxacin, levofloxacin, gatifloxacin, grepafloxacin, moxifloxacin, delafloxacin, nemonoxacin, zabofloxacin, ozenoxacin, chinfloxacin, JNJ-Q2, DS-8587, KPI-10, GSK2140944, ACH-702 and finafloxacin, as well as oxazolidinones such as linezolid, tedizolid and radezolid (especially linezolid or moxifloxacin) are used as further antibacterial compound (ii), it is preferred that the corresponding pharmaceutical compositions and/or the combinations of the present invention are used for the treatment or prophylaxis of bacterial infections in particular those caused by β-lactam-, quinolone- (including fluoroquinolone-), oxazolidinone- and/or multi-drug-resistant bacteria. Such infections include cardiovascular, central nervous system, circulatory, gastrointestinal, genitourinary, intra-abdominal, lower/upper respiratory, skeletal (bones and joints), and skin and soft tissue infections including diabetic foot.

According to a further preferred embodiment, the at least one further antibacterial compound (ii) is selected from the following compounds: β-lactams such as amoxicillin, ampicillin, penicillin G (benzylpenicillin), penicillin V (phenoxymethylpenicillin), piperacillin, mezlocillin, azlocillin, oxacillin, cloxacillin, dicloxacillin, flucloxacillin, sultamicillin, carbenicillin, temocillin, ticarcillin, imipenem, meropenem, ertapenem, faropenem, biapenem, cefazolin, cefepime, cefotaxime, cefoxitine, ceftaroline, ceftazidime, ceftobiprole, ceftriaxone, cefuroxime and cephalexine, aztreonam and BAL30072 as well as combinations of β-lactams with a β-lactamase inhibitor such as clavulanic acid+amoxicillin, sulbactam+ampicillin, tazobactam+piperacillin, ticarcillin+clavulanate, ceftazidime+avibactam, ceftaroline+avibactam, imipenem+MX-7655, biapenem+RPX7009, and aztreonam+avibactam.

Further especially preferably, the at least one further antibacterial compound (ii) is selected from the following compounds: ampicillin and ceftriaxone.

If β-lactams such as amoxicillin, ampicillin, penicillin G (benzylpenicillin), penicillin V (phenoxymethylpenicillin), piperacillin, mezlocillin, azlocillin, oxacillin, cloxacillin, dicloxacillin, flucloxacillin, sultamicillin, carbenicillin, temocillin, ticarcillin, imipenem, meropenem, ertapenem, faropenem, biapenem, cefazolin, cefepime, cefotaxime, cefoxitine, ceftaroline, ceftazidime, ceftobiprole, ceftriaxone, cefuroxime and cephalexine, aztreonam and BAL30072 or combinations of β-lactams with a β-lactamase inhibitor such as clavulanic acid+amoxicillin, sulbactam+ampicillin, tazobactam+piperacillin, ticarcillin+clavulanate, ceftazidime+avibactam, ceftaroline+avibactam, imipenem+MX-7655, biapenem+RPX7009, and aztreonam+avibactam (especially ampicillin or ceftriaxone) are used as further antibacterial compound (ii), it is preferred that the corresponding pharmaceutical compositions and/or the combinations of the present invention are used for the treatment or prophylaxis of bacterial infections in particular those caused by β-lactam- and/or multi-drug resistant Gram-positive bacteria, including but not limited to methicillin-resistant staphylococci (e.g. MRSA, MRSE) and/or penicillin-resistant streptococci (e.g. PRSP), and/or multi-drug-resistant and/or -vancomycin-resistant enterococci. Such infections include cardiovascular, central nervous system, circulatory, gastrointestinal, genitourinary, intra-abdominal, lower/upper respiratory, skeletal (bones and joints), and skin and soft tissue infections including diabetic foot.

According to a further preferred embodiment, the at least one further antibacterial compound (ii) is selected from the following compounds: vancomycin, daptomycin, tobramycin, ciprofloxacin, tigecycline, imipenem, piperacillin-tazobactam, telavancin, dalbavancin, oritavancin and ceftazidime.

If vancomycin, daptomycin, tobramycin, ciprofloxacin, tigecycline, imipenem, piperacillin-tazobactam, telavancin, dalbavancin, oritavancin or ceftazidime are used as further antibacterial compound (ii), it is preferred that the corresponding pharmaceutical compositions and/or the combinations of the present invention are used for the treatment or prophylaxis of bacterial infections. In particular, such infections include cardiovascular, central nervous system, circulatory, gastrointestinal, genitourinary, intra-abdominal, lower/upper respiratory, skeletal (bones and joints), and skin and soft tissue infections including diabetic foot.

According to a further preferred embodiment, the at least one further antibacterial compound (ii) is selected from the following compounds: fosfomycin and other cell wall synthesis inhibitors, such as β-lactams, e.g. amoxicillin, penicillin G (benzylpenicillin), penicillin V (phenoxymethylpenicillin), piperacillin, mezlocillin, azlocillin, oxacillin, cloxacillin, dicloxacillin, flucloxacillin, sultamicillin, carbenicillin, temocillin, ticarcillin, imipenem, meropenem, ertapenem, faropenem, biapenem, cefazolin, cefepime, cefotaxime, cefoxitine, ceftaroline, ceftazidime, ceftobiprole, ceftriaxone, cefuroxime and cephalexine, aztreonam, BAL30072 as well as combinations of β-lactams with a β-lactamase inhibitor such as clavulanic acid+amoxicillin, sulbactam+ampicillin, tazobactam+piperacillin, ticarcillin+clavulanate, ceftazidime+avibactam, ceftaroline+avibactam, imipenem+MX-7655, biapenem+RPX7009, and aztreonam+avibactam.

Further especially preferably, the further antibacterial compound (ii) is fosfomycin.

If fosfomycin or other cell wall synthesis inhibitors, such as β-lactams, e.g. amoxicillin, penicillin G (benzylpenicillin), penicillin V (phenoxymethylpenicillin), piperacillin, mezlocillin, azlocillin, oxacillin, cloxacillin, dicloxacillin, flucloxacillin, sultamicillin, carbenicillin, temocillin, ticarcillin, imipenem, meropenem, ertapenem, faropenem, biapenem, cefazolin, cefepime, cefotaxime, cefoxitine, ceftaroline, ceftazidime, ceftobiprole, ceftriaxone, cefuroxime and cephalexine, aztreonam, BAL30072 or combinations of β-lactams with a β-lactamase inhibitor such as clavulanic acid+amoxicillin, sulbactam+ampicillin, tazobactam+piperacillin, ticarcillin+clavulanate, ceftazidime+avibactam, ceftaroline+avibactam, imipenem+MX-7655, biapenem+RPX7009, and aztreonam+avibactam (especially fosfomycin) are used as further antibacterial compound (ii), it is preferred that the corresponding pharmaceutical compositions and/or the combinations of the present invention are used in particular for the treatment or prophylaxis of bacterial infections caused by Gram-negative bacteria such as Enterobacteriaceae and non-fermenters including but not limited to ESBL- and/or AmpC producing isolates as well as by Gram-positive bacteria including but not limited to multi-drug- and/or methicillin-resistant staphylococci (e.g. MRSA or MRSE), multi-drug- and/or penicillin-resistant streptococci (e.g. PRSP), and multi-drug- and/or vancomycin-resistant enterococci (e.g. VRE).

According to a further especially preferred embodiment, the present invention provides a combination and/or a pharmaceutical composition and/or a kit-of-parts comprising:
i) an oxazolidinone-quinolone hybrid and
ii) colistin,
wherein the oxazolidinone-quinolone hybrid is selected from the following compounds: 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid, and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to a further especially preferred embodiment, the present invention provides a combination and/or a pharmaceutical composition and/or a kit-of-parts comprising:
i) an oxazolidinone-quinolone hybrid and
ii) linezolid,
wherein the oxazolidinone-quinolone hybrid is selected from the following compounds: 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid, and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to a further especially preferred embodiment, the present invention provides a combination and/or a pharmaceutical composition and/or a kit-of-parts comprising:
i) an oxazolidinone-quinolone hybrid and
ii) moxifloxacin,
wherein the oxazolidinone-quinolone hybrid is selected from the following compounds: 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid, and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to a further especially preferred embodiment, the present invention provides a combination and/or a pharmaceutical composition and/or a kit-of-parts comprising:
i) an oxazolidinone-quinolone hybrid and
ii) ampicillin,
wherein the oxazolidinone-quinolone hybrid is selected from the following compounds: 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid, and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to a further especially preferred embodiment, the present invention provides a combination and/or a pharmaceutical composition and/or a kit-of-parts comprising:
i) an oxazolidinone-quinolone hybrid and
ii) ceftriaxone,
wherein the oxazolidinone-quinolone hybrid is selected from the following compounds: 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid, and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to a further especially preferred embodiment, the present invention provides a combination and/or a pharmaceutical composition and/or a kit-of-parts comprising:
i) an oxazolidinone-quinolone hybrid and
ii) fosfomycin,
wherein the oxazolidinone-quinolone hybrid is selected from the following compounds: 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid, and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid or a salt thereof, such as e.g.: the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid.

According to a further especially preferred embodiment, the present invention provides a combination and/or a pharmaceutical composition and/or a kit-of-parts comprising:
i) 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid; and
ii) colistin.

According to a further especially preferred embodiment, the present invention provides a combination and/or a pharmaceutical composition and/or a kit-of-parts comprising:
i) 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid; and
ii) linezolid.

According to a further especially preferred embodiment, the present invention provides a combination and/or a pharmaceutical composition and/or a kit-of-parts comprising:
i) 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid; and
ii) moxifloxacin.

According to a further especially preferred embodiment, the present invention provides a combination and/or a pharmaceutical composition and/or a kit-of-parts comprising:
i) 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid; and
ii) ampicillin.

According to a further especially preferred embodiment, the present invention provides a combination and/or a pharmaceutical composition and/or a kit-of-parts comprising:
i) 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid; and
ii) ceftriaxone.

According to a further especially preferred embodiment, the present invention provides a combination and/or a pharmaceutical composition and/or a kit-of-parts comprising:
i) 7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid; and
ii) fosfomycin.

According to a further especially preferred embodiment, the present invention provides a combination and/or a pharmaceutical composition and/or a kit-of-parts comprising:
i) the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid; and
ii) colistin.

According to a further especially preferred embodiment, the present invention provides a combination and/or a pharmaceutical composition and/or a kit-of-parts comprising:
i) the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid; and
ii) linezolid.

According to a further especially preferred embodiment, the present invention provides a combination and/or a pharmaceutical composition and/or a kit-of-parts comprising:
i) the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid; and
ii) moxifloxacin.

According to a further especially preferred embodiment, the present invention provides a combination and/or a pharmaceutical composition and/or a kit-of-parts comprising:
i) the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid; and
ii) ampicillin.

According to a further especially preferred embodiment, the present invention provides a combination and/or a pharmaceutical composition and/or a kit-of-parts comprising:
i) the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid; and
ii) ceftriaxone.

According to a further especially preferred embodiment, the present invention provides a combination and/or a pharmaceutical composition and/or a kit-of-parts comprising:
i) the sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid; and
ii) fosfomycin.

The present invention also encompasses pharmacologically acceptable salts, or solvates and hydrates, respectively of compounds (i) and (ii).

Examples of pharmacologically acceptable salts of sufficiently basic compounds (i) or (ii) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound (i) or (ii) may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts. Compounds (i) or (ii) may be solvated, especially hydrated. The hydratisation can occur during the process of production or as a consequence of the hygroscopic nature of initially water free compounds (i) or (ii).

The combinations according to the invention include at least two active compounds, which can be administered simultaneously, separately or spread over time. They can for example be provided in kit form (e.g. as kit-of-parts), allowing the administration of an oxazolidinone-quinolone hybrid (compound i) and that of the further antibacterial agent (compound ii) separately.

The weight ratio of the oxazolidinone-quinolone hybrid (compound i) to the further antibacterial compound (compound ii) may range from 999:1 to 1:999.

Preferably, the weight ratio of the oxazolidinone-quinolone hybrid (compound i) to the further antibacterial compound (compound ii) is from 99:1 to 1:99.

The pharmaceutical compositions according to the present invention contain an oxazolidinone-quinolone hybrid (e.g. a compound of formula (I) or (II)) and a further antibacterial compound. The pharmaceutical compositions optionally further contain carriers and/or diluents and/or adjuvants. Optionally the pharmaceutical compositions according to the present invention may also contain further additional antibacterial compounds.

The combinations (e.g. the pharmaceutical compositions) according to the present invention may be administered by using the known and acceptable modes known in the art, either alone or in combination with any other therapeutic agent. They can e.g. be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal or locally by topical application for example as ointment, paste, drops, lotion, solution, e.g. on the skin, mucosa, eye, or ear, or in the oral cavity, abdominal cavity, or pleural cavity. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatin, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions (e.g. drops), emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilisation, e.g. UV stabilizers, emulsifiers, sweetener, aromatisers, salts to change the osmotic pressure, buffers, coating additives and antioxidants.

A daily dosage per patient of about 1 mg to about 10 g of the combination (e.g. the composition) of the present invention, especially about 50 mg to 3 g is usual with those of ordinary skill in the art appreciating that the dosage will depend also upon the age, conditions of the subject to be treated, and the kind of diseases being treated or prevented. The daily dosage can be administered in a single dose or can be divided over several doses. An average single dose of about 50 mg, 100 mg, 250 mg, 500 mg, 1000 mg and 2000 mg can be contemplated. The inventive combinations can also be used as disinfectants for surgical instruments.

EXAMPLES

1. Materials and Methods 1.1 MIC Determinations and Time-Kill Assays

Minimal inhibitory concentrations (MICs) of compound 1 for the test strains and quality-control strains (see Section 1.3) were determined in duplicate on separate occasions by the broth microdilution method according to CLSI guidelines (Clinical and Laboratory Standards Institute (CLSI); M07-A8 Methods for dilution antimicrobial susceptibility testing for bacteria that grow aerobically: approved standard; 8th edition 2009; Clinical and Laboratory Standards Institute, Wayne, Pa.) with cation-adjusted Mueller Hinton-broth (CAMHB). Two-fold serial dilutions (256 to 0.03 mg/L) in CAMHB using 10 mL plastic tubes were dispensed into empty round bottom 96-well plates.

MIC-testing was done immediately after preparation of the dilutions. All tests were done in duplicate and repeated once on a separate occasion. Data reported in the results chapter (see Section 2) represent the higher MIC-values in case of deviating data, which were recorded rarely.

Unexposed test strains served as growth controls. Moxifloxacin was used as a quality control drug. *S. aureus* ATCC 29213, *E. faecalis* ATCC 29212, *S. pneumoniae* ATCC 49619 and 33400, *E. coli* ATCC 25922, and *P. aeruginosa* ATCC 10145 served as quality control strains as recommended by CLSI guidelines. In general, all the quality controls were within the acceptable limits in every run not only for the control drug moxifloxacin, but for all other antibacterial agents tested (see Section 1.2) as well.

Kill-curve kinetics were determined in duplicate according to CLSI guidelines (Clinical and Laboratory Standards Institute (CLSI); M07-A8 Methods for dilution antimicrobial susceptibility testing for bacteria that grow aerobically: approved standard; 8th edition 2009; Clinical and Laboratory Standards Institute, Wayne, Pa.). Samples for quantification of viable counts were withdrawn at 0, 1, 2, 4, 6, 8, and 24 hours.

Single-point kill rates (k) were calculated as previously described (Schaper K. J., Schubert S., Dalhoff A. Kinetics and quantification of antimicrobial effects of beta-lactams, macrolides, and quinolones against Gram-positive and Gram-negative RTI-pathogens. Infection 2005; 33 (Suppl 2): 3-14) using the following equation (with $N_o$ and $N_t$=viable counts at times 0 h and t):

$$k^{(h-1)} = (\ln(N_t/N_0))/t$$

1.2 Oxazolidinone-Quinolone Hybrid (Compound 1) and Combination Agents

Compound 1:

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

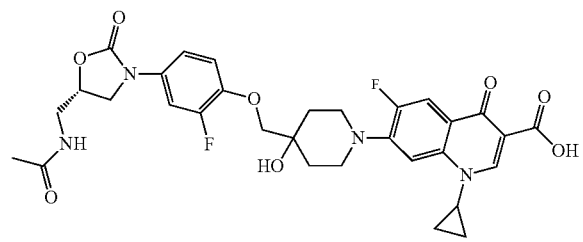 [SMILES: CC(=O)NC[C@H]1CN(c2ccc(OCC3(O)CCN(c4cc5c(cc4F)c(=O)c(C(=O)O)cn5C4CC4)CC3)c(F)c2)C(=O)O1]

This compound was prepared according to the procedure described in WO 2005/058888. For the following tests, Compound 1 was dissolved and diluted in DMSO.

The following antibacterial agents were selected as combination agents (i.e. antibacterial compound ii; hereinafter also "Combination Agent(s)") based on their antibacterial spectrum and therapeutic use in difficult to treat bacterial infections with Gram-positive and Gram-negative pathogens:

Colistin CF 80 mg powder=33.3 mg pure colistin, Gruenenthal GmbH, & Co KG, 52078 Aachen, Germany (Batch No. 111C06)
Fosfomycin, fosfocina, 4 g infusion-solution, Laboratorios ERN, S.A., E-8020 Barcelona, Spain (Batch No. E014)
Ciprofloxacin Kabi, 400 mg/200 mL infusion-solution, Fresenius Kabi Deutschland GmbH, D-61352 Bad Homburg, Germany, (Batch No. 15FC145F2)
Moxifloxacin, Bayer Vital GmbH, D-51368 Leverkusen, Germany (Batch No. BXGON82)
Ampicillin, 1.06 g powder=1.0 g pure substance, Ratiopharm, D-89079 Ulm, Germany, (Batch No. L46849)
Ceftazidime, Fortum 2.0 g, 2.606 g powder=2.328 g pure substance, MIP Pharma, D-66440 Blieskastel (Batch No. 1012)
Ceftriaxone, Ceftriaxon-saar, 1.193 g powder=1.0 g pure substance, MIP Pharma, D-66440 Blieskastel (Batch No. 2355000)
Imipenem, Zienam 500 mg/500 mg (imipenem+cilastatin), MSD Sharp & Dohme GmbH, D-85540 Haar, Germany (Batch No. 2050470)
Piperacillin/tazobactam, Tazobac EF 4 g/0.5 g, Pfizer Pharma GmbH, D-10785 Berlin (Batch No. AH2R/21)
Daptomycin, Cubicin 500 mg, infusion solution, Novartis Europharm Ltd., RH12 5AB Horsham, UK (Batch No. CDC153D)
Linezolid, Zyvoxid 2 mg/mL infusion-solution, Pfizer Pharma GmbH, D-10785 Berlin (Batch No. 12B08U10)
Tobramycin, Gernebcin 80 mg/2 mL infusion-solution, Infectopharm Arzneimittel und Consilium GmbH, D-64630 Heppenheim (Batch No. W081102.1)
Vancomycin, vancomycin CP 500 mg, 512 mg powder=500 mg pure substance, Hikma Pharma GmbH, D-82166 Grifelfing (Batch No. 111204.1)
Tigecycline, Tygacil 50 mg infusion-solution, Wyeth Europe Ltd. Berks SL6 0PH, UK (Batch No. F75592)

1.3 Test and Quality Control Strains

The bacterial strains studied were selected based on their antibacterial susceptibility patterns expressing specific, difficult to treat resistance mechanisms; they do not represent current clinically and epidemiologically relevant strains causing respiratory tract or skin and soft tissue infections or other infectious diseases.

In general, one susceptible wild-type strain per species was included into the panel of test strains. This susceptible strain was most frequently identical with the ATCC quality control strains mentioned in Section 1.1; the additional ATCC susceptible wild-type strains are mentioned below:

Gram-Negative Bacteria:
E. coli ATCC 25922 (quality control for MIC-testing)
E. coli NRZ-00401 (metallo β-lactamase VIM-1)
E. coli NRZ-00302 (metallo β-lactamase NDM-1)
E. coli GNS-2601 (ESBL CTX-M-15)
K. pneumoniae ATCC 13883 quality control for MIC-testing)
K. pneumoniae NRZ-00002 (OXA-48)
K. pneumoniae NRZ-00535 (VIM-1)
K. pneumoniae NRZ-00103 (KPC-2)
P. mirabilis ATCC 9240 (susceptible wild type)
P. mirabilis NRZ-00185 (AmpC, type CMY-2)
P. aeruginosa ATCC 10145 (quality control for MIC-testing)
P. aeruginosa NRZ-00425 (VIM-1)
E. cloacae ATCC 13047 (susceptible wild type)
E. cloacae NRZ-00239 (VIM-1)
Gram-Positive Bacteria:
S. aureus ATCC 29213 (quality control for kill curve assays)
S. aureus RNG1GH 001 (quality control for kill curve assays)
S. aureus DSM 11823, clone 16 (MSSA, quinolone-resistant)
S. aureus ATCC 33593 (MRSA)
S. aureus NRS-119 (MRSA, linezolid- and quinolone-resistant)
S. aureus Visa Mu 50 (MRSA, vancomycin intermediate susceptible)
E. faecalis ATCC 29212 (quality control)
E. faecalis V583 (VanB)
E. faecium DSMZ 2146 (susceptible wild type)

E. faecium UW 3695 (linezolid and quinolone-resistant)
S. pneumoniae ATCC 49619 (quality control for MIC-testing)
S. pneumoniae ATCC 33400 (susceptible wild type)
S. pneumoniae BAY 19397 (penicillin-, macrolide-, quinolone-resistant)

1.4 Media

Cation adjusted Mueller-Hinton Broth (CAMHB) (Becton-Dickinson-Diagnostics, D-69126 Heidelberg, Germany) was used.

1.5 Preparation of Inoculum

Test strains were subcultured on columbia agar and incubated overnight at 36° C.+/−1° C.

A tube containing 3-5 mL sterile 0.85% NaCl was inoculated with five or more colonies from the agar plate and adjusted to a turbidity equivalent to a No. 0.5 McFarland standard ($1\times10^8$ CFU/mL).

1 mL of the bacterial suspension was transferred into a tube containing 10 mL CAMHB and was vortexed thoroughly. (S. pneumoniae 1 mL in 10 mL CAMHB+5% lysed horse blood). Columns 1-15 of the 96-well plate were inoculated with 5 µL of this suspension (1-15=antibacterial solution, 16=sterile medium without test item).

The plates were shaken carefully for ca. 5 min and then incubated 18-24 hours at 36° C.

Turbidity was read visually with a mirror.

Final volume: 105 µL (antibacterial solution 100 µL, bacterial suspension 5 µL)

Final bacterial concentration: $5\times10^5$ CFU/mL

Final antimicrobial concentrations: 0.06-16 mg/L 1.6 Synergy Tests and FIC Index Synergy tests were performed by three methods (Neu H. C., Fu K. P. Synergy of azlocillin and mezlocillin combined with aminoglycoside antibiotics and cephalosporins. Antimicrob Agents Chemother 1978; 13 (5): 813-819):

1. One Combination Agent was added in a concentration equivalent to one-half (0.5) its minimal inhibitory concentration (MIC) to increasing concentrations of Compound 1.
2. Killing curve techniques were used to evaluate the combination of one Combination Agent and COMPOUND 1 in concentrations equivalent to 1+1, 1+2, 2+1, and 2+2 times of their MICs. Time-kill studies were performed by adding the combined antibacterials to log-phase E. coli cultures (10 mL) diluted to $10^5$-$10^6$ CFU/mL and growing in 50-mL flasks at 37° C.
3. A checkerboard twofold-dilution method with one Combination Agent and Compound 1 per assay was used (Pillai, S., Moellering R., Eliopoulos G. Antimicrobial combinations, In V. Lorian (ed.), Antibiotics in laboratory medicine, 5th ed. Lippincott Williams & Wilkins, Baltimore, Md., 2005, pp. 365-440).

Checkerboard Technique, Fractional Inhibitory Concentration (FIC), and FIC Index:

The broth microdilution bactericidal checkerboard method was used as described previously (Pillai, S., Moellering R., Eliopoulos G. Antimicrobial combinations, In V. Lorian (ed.), Antibiotics in laboratory medicine, 5th ed. Lippincott Williams & Wilkins, Baltimore, Md., 2005, pp. 365-440). Serial dilutions of the two antibacterials A and B (i.e. one Combination Agent and Compound 1) were tested. The checkerboard consists of columns in which each well contains the same amount of antibacterial A being over i dilutions along the x-axis, and in rows in which each well contains the same amount of antibacterial B over j dilutions on the y-axis, i.e. serial dilutions of antibacterials A and B, respectively, are titrated in a rectangular fashion. The result is that each well contains a different combination of the two antibacterials, so that each concentration of antibacterial A is combined with every concentration of antibacterial B. Growth and sterility controls were included in all plates. A bacterial inoculum of $5\times10^5$ CFU/mL (prepared as described above) was used. Microtiter trays were incubated at 37° C. for 18 hours.

The fractional inhibitory concentration (FIC) is a mathematical expression of the effect of the combination of two antibacterial agents A and B. The FICs were calculated as the MIC of antibacterial A and antibacterial B in combination divided by the MIC of antibacterial A or antibacterial B alone. The FIC index is considered to specify whether the combination had a synergistic, additive, indifferent, or antagonistic effect (Terminology relating to methods for the determination of susceptibility of bacteria to antimicrobial agents. European Committee for Antimicrobial Susceptibility testing (EUCAST) of the European Society for Clinical Microbiology and Infectious Diseases (ESCMID). EUCAST definitive document E.Def 1.2; Clin Microbiol Infect Dis 2000; 6:503-508):

Synergism was defined as an FIC index of less than 0.5.
Additive or indifferent effects were defined as an FIC index of 0.5-4 (additive effects >0.5-1; indifference >1-4).
Antagonism was defined as an FIC index of more than 4.

The FICs and FIC index, respectively, are calculated according to the following equations:

$$FIC_{(A)} = MIC_{(A\ in\ the\ presence\ of\ B)} / MIC_{(A\ alone)}$$

$$FIC_{(B)} = MIC_{(B\ in\ the\ presence\ of\ A)} / MIC_{(B\ alone)}$$

$$FIC\ index = FIC_{(A)} + FIC_{(B)}$$

2. Results 2.1 Quality Controls

The internationally accepted strains E. coli ATCC 25922, K. pneumoniae ATCC 13883, and P. aeruginosa ATCC 10145 served as quality control strains for susceptibility testing. The MICs of the various agents tested for these quality control strains were within the accepted limits as defined by CLSI.

In addition to the ATCC-reference strains used as quality controls for MIC-testing, S. aureus ATCC 29213 and S. aureus RNG1GH 001 were used as quality controls for the time-kill experiments. S. aureus ATCC 29213 was exposed to moxifloxacin on seven different occasions during this study; moxifloxacin was chosen as a reference drug. Furthermore, the Compound 1—susceptible strain S. aureus RN1GH 001 was exposed to different concentrations of Compound 1 on different occasions, so that the reproducibility of the antibacterial effect of Compound 1 could be assessed.

2.2 MIC-Testing of Compound 1 in the Presence of Combination Agents

The values presented below in Tables 1A to 1C and 2A to 2C represent either the MICs of the corresponding monosubstances, or—in case of combination tests—the MICs of Compound 1 only, as the combination tests have been performed with subinhibitory concentrations of the various Combination Agents corresponding to 0.5 of their respective MICs (see Section 1.6), thus not generating MICs for the individual Combination Agents.

Experiments reported in Table 1A have been repeated three times; all other tests reported in Tables 1B and 1C, and Tables 2A, 2B and 2C have been repeated once.

Activity Against Gram-Negatives (See Tables 1A, B, and C):

Colistin, Fosfomycin:

Compound 1 shows low activity against Enterobacteriaceae or non-fermenters. Colistin is active against Enterobacteriaceae but not against the *P. aeruginosa* strains tested. Fosfomycin has been tested against *E. coli* only against which it exhibits heterogeneous activity.

The combination of Compound 1 with colistin reduced the MICs of Compound 1 against Enterobacteriaceae by 6 or even 9 titration steps (Table 1A).

The combination of Compound 1 with fosfomycin reduced the MICs of Compound 1 by two to three titrations steps against two *E. coli* and >9 titration steps against the remainder *E. coli* test strains (Table 1A).

TABLE 1A

Antibacterial activity (MIC in mg/L) of the monosubstances Compound 1, colistin, and fosfomycin, or Compound 1 in combination with 0.5-times the MICs of colistin and fosfomycin, respectively

| Strain | Compound 1 | colistin | MCB + colistin | fosfo | MCB + fosfo |
|---|---|---|---|---|---|
| Ec ATCC25922 | 16 | 1 | <0.25 | 2 | 2 |
| Ec NRZ00401 | 16 | 1 | <0.25 | 2 | 4 |

TABLE 1A-continued

Antibacterial activity (MIC in mg/L) of the monosubstances Compound 1, colistin, and fosfomycin, or Compound 1 in combination with 0.5-times the MICs of colistin and fosfomycin, respectively

| Strain | Compound 1 | colistin | MCB + colistin | fosfo | MCB + fosfo |
|---|---|---|---|---|---|
| Ec NRZ00302 | 256 | 1 | <0.25 | 64 | 0.5 |
| Ec GNS2601 | 256 | 2 | <0.25 | 64 | <0.25 |
| Kp ATCC13883 | 128 | 0.03 | >128 | nt | nt |
| Kp NRZ00002 | 256 | 0.25 | >128 | nt | nt |
| Kp NRZ00535 | >256 | 0.25 | >128 | nt | nt |
| Kp NRZ00103 | 256 | 0.25 | >128 | nt | nt |
| Pm ATCC9240 | 256 | >256 | nt | nt | nt |
| Pm NRZ00185 | 256 | >256 | nt | nt | nt |
| Pa ATCC10145 | 256 | 0.5 | >128 | nt | nt |
| Pa NRZ00425 | 256 | 1 | >128 | nt | nt |
| Ecl ATCC13047 | 128 | 64 | 1 | nt | nt |
| Ecl NRZ00239 | 256 | 0.5 | >128 | nt | nt |

(Ec = *E. coli*; Kp = *K. pneumoniae*; Pm = *P. mirabilis*; Pa = *P. aeruginosa*; Ecl = *E. cloacae*; MCB = Compound 1; fosfo = fosfomycin; nt = not tested)

Tobramycin, Ciprofloxacin, Tigecycline:

Tobramycin was active against the susceptible wild type strains only as well as against the CMY-2 producing *P. mirabilis* strain; the tobramycin MIC exceeded 4 mg/L against the remainder test strains. Ciprofloxacin was active against the wild type strains and against two of the β-lactamase producing strains (*E. coli* NRZ-00401 and *P. mirabilis* NRZ-00103). The ciprofloxacin MICs exceeded 16 mg/L against the remaining strains. The combination of Compound 1 with ciprofloxacin reduced the MICs of Compound 1 of all the test strains. The MICs of Compound 1 of the wild type strains were remarkably reduced, whereas the MICs of Compound 1 of the selected resistant strains were not affected (Table 1B). Tigecycline inhibited the reference strain *E. coli* ATCC 25922 at 0.5 mg/L; all the other strains tested were inhibited by tigecycline concentrations >2 mg/L. The combination of Compound 1 plus tigecycline did not affect the activity of Compound 1 against these Gram-negative test strains (Table 1B).

TABLE 1B

Antibacterial activity (MIC in mg/L) of the monosubstances Compound 1, tobramycin, ciprofloxacin, and tigecycline, or Compound 1 in combination with 0.5-times the MICs of tobramycin, ciprofloxacin, and tigecycline, respectively

| Strain | MCB | tob | MCB + tob | cip | MCB + cip | tige | MCB + tige |
|---|---|---|---|---|---|---|---|
| Ec ATCC25922 | 16 | 1 | 0.5 | 0.004 | 4 | 0.5 | 16 |
| Ec NRZ00401 | 16 | 4 | 16 | 0.015 | 0.0005 | 2 | 32 |
| Ec NRZ00302 | 256 | 64 | 64 | 128 | >128 | 2 | >128 |
| Ec GNS2601 | 256 | 32 | 16 | 32 | >128 | 4 | >128 |
| Kp ATCC13883 | 128 | 0.125 | 64 | 0.03 | 32 | 2 | 256 |
| Kp NRZ00002 | 256 | 16 | 256 | 128 | 256 | 2 | >256 |
| Kp NRZ00535 | >256 | 8 | 256 | 128 | 256 | 2 | >256 |
| Kp NRZ00103 | 256 | 16 | 256 | 128 | 256 | 4 | >256 |
| Pm ATCC9240 | 256 | 0.5 | 128 | 0.015 | 16 | 8 | 128 |
| Pm NRZ00185 | 256 | 0.125 | 256 | 0.06 | 128 | 8 | 256 |
| Pa ATCC10145 | 256 | 0.5 | 128 | 0.5 | <0.0005 | 16 | 512 |
| Pa NRZ00425 | 256 | >128 | nt | 32 | 512 | 32 | 512 |
| Ecl ATCC13047 | 128 | 0.25 | 64 | 0.015 | 0.125 | 2 | 512 |
| Ecl NRZ00239 | 256 | 4 | 128 | 16 | 512 | 2 | 512 |

(Ec = *E. coli*; Kp = *K. pneumoniae*; Pm = *P. mirabilis*; Pa = *P. aeruginosa*; Ecl = *E. cloacae*; MCB = Compound 1; tob = tobramycin; cip = ciprofloxacin; tige = tigecycline)

Imipenem, Piperacillin/Tazobactam, Ceftazidime:

Among the β-lactams tested, imipenem was the most active one; it inhibited all the test strains except *P. aeruginosa* NRZ-00185 and *K. pneumoniae* NRZ-00103 at concentrations <8 mg/L (Table 1C). The combination of Compound 1 with imipenem did not affect the MICs of Compound 1. Piperacillin/tazobactam was active against the wild type *E. coli, K. pneumoniae,* and *P. mirabilis* strains; the MICs of the remainder strains were >4 mg/L. The combination of Compound 1 with piperacillin/tazobactam reduced the MICs of three test strains (*E. coli* ATCC 25922, *E. coli* GNS2601; *P. aeruginosa* ATCC 10145) by two to three dilution steps, but did not affect the activity of Compound 1 against the other test strains. Ceftazidime inhibited the *E. coli, K. pneumoniae,* and *P. mirabilis* wild type strains at low concentrations of <0.5 mg/L; the MICs of the remainder strains exceeded 2 mg/L. The combination of Compound 1 with ceftazidime resulted in a pronounced activity against the two *P. aeruginosa* strains, but did not affect the activity of Compound 1 against the other test strains (Table 1C).

0.06 to <0.00003 mg/L, respectively; the MIC of Compound 1 for *E. faecium* DSMZ 2146, too, was reduced from 0.06 to <0.00003 mg/L. The MIC of Compound 1 for *S. pneumoniae* 19397 in combination with ceftriaxone was reduced from 0.004 to <0.00003 mg/L (Table 2A).

TABLE 2A

Antibacterial activity (MIC in mg/L) of the monosubstances Compound 1, ampicillin, and ceftriaxone, or Compound 1 in combination with 0.5-times the MICs of ampicillin, and ceftriaxone

| Strain | MCB | ampi | MCB + ampi | ceftr | MCB + ceftr |
|---|---|---|---|---|---|
| Sa ATCC29213 | 0.25 | 0.5 | 0.125 | 4 | 0.125 |
| Sa clone16 | 0.03 | 0.007 | 0.015 | 4 | 0.125 |
| Sa ATCC33593 | 0.03 | 64 | 0.125 | >256 | 0.125 |
| Sa NRS119 | 1 | 128 | 0.25 | >256 | 1 |
| Sa VisaMu50 | 0.06 | 256 | <0.00003 | 16 | 0.5 |
| Ef ATCC29212 | 0.03 | 1 | 0.125 | 0.5 | 0.25 |
| Ef V583 | 0.03 | 0.5 | 0.125 | 0.5 | 0.125 |
| Efc DSMZ2146 | 0.06 | 128 | <0.00003 | 0.5 | 0.125 |
| Efc UW3695 | 0.06 | 32 | 0.25* | 32 | 1 |

TABLE 1C

Antibacterial activity (MIC in mg/L) of the monosubstances Compound 1, imipenem, piperacillin/tazobactam, and ceftazidime, or Compound 1 in combination with 0.5-times the MICs of imipenem, piperacillin/tazobactam, and ceftazidime, respectively

| Strain | MCB | imi | MCB + imi | P/T | MCB + P/T | cef | MCB + cef |
|---|---|---|---|---|---|---|---|
| Ec ATCC25922 | 16 | 0.03 | 16 | 2 | 4 | 0.03 | 8 |
| Ec NRZ00401 | 16 | 4 | 8 | 64 | 32 | 32 | 32 |
| Ec NRZ00302 | 256 | 4 | >128 | 256 | 128 | >256 | >128 |
| Ec GNS2601 | 256 | 0.03 | >128 | 64 | 64 | 128 | 128 |
| Kp ATCC13883 | 128 | 0.25 | 128 | 2 | >128 | 0.25 | >256 |
| Kp NRZ00002 | 256 | 2 | >128 | >256 | 128 | 64 | >256 |
| Kp NRZ00535 | >256 | 8 | >128 | >256 | >128 | >256 | >256 |
| Kp NRZ00103 | 256 | 32 | nt | >256 | >128 | >256 | >256 |
| Pm ATCC9240 | 256 | 1 | 128 | 0.5 | >128 | 0.5 | 128 |
| Pm NRZ00185 | 256 | 1 | >128 | 4 | >128 | 128 | 128 |
| Pa ATCC10145 | 256 | 0.5 | 128 | 8 | 32 | 2 | <0.0001 |
| Pa NRZ00425 | 256 | 128 | >128 | 64 | >128 | 32 | <0.0001 |
| Ecl ATCC13047 | 128 | 0.25 | 128 | 8 | 128 | 2 | 128 |
| Ecl NRZ00239 | 256 | 0.25 | >128 | 8 | >128 | 4 | >128 |

(Ec = *E. coli*; Kp = *K. pneumoniae*; Pm = *P. mirabilis*; Pa = *P. aeruginosa*; Ecl = *E. cloacae*; MCB = Compound 1; imi = imipenem; P/T = piperacillin/tazobactam; cef = ceftazidime; * = these data were reproducible twice, but variable on the other occasion; nt = not tested)

Activity Against Gram-Positives (See Tables 2A, B, and C):

Compound 1 was active against all Gram-positive strains tested irrespective of their susceptibility patterns; the wild type strains were inhibited equally well as the multidrug resistant strains by Compound 1 concentrations of <0.25 mg/L (Tables 2A to 2C).

Ampicillin, Ceftriaxone:

The β-lactams ampicillin and ceftriaxone were active against the wild type- or MSSA-strains only (Table 2A). Compound 1 in combination with both β-lactams was within the accepted range of variability (+/–one to two titration steps) as active as Compound 1 alone against most of the test strains except the MRSA strains NRS-119 and Visa Mu 50 in combination with amipicillin, for which the MICs of Compound 1 were reduced from 1 to 0.25 mg/L, and from TABLE 2A-continued Antibacterial activity (MIC in mg/L) of the monosubstances Compound 1, ampicillin, and ceftriaxone, or Compound 1 in combination with 0.5-times the MICs of ampicillin, and ceftriaxone

| Strain | MCB | ampi | MCB + ampi | ceftr | MCB + ceftr |
|---|---|---|---|---|---|
| Spn ATCC33400 | 0.0075 | 0.0075 | 0.125 | 0.0075 | 0.125 |
| Spn 19397 | 0.0004 | 1 | 0.03 | 4 | <0.00003 |

(MCB = Compound 1; ampi = ampicillin; ceftr = ceftriaxone; Sa = *S. aureus*; Ef = *E. faecalis*; Efc = *E. faecium*; Spn = *S. pneumoniae*; *= these data were reproducible twice, but variable on the other occasion)

Vancomycin, Daptomycin:

Vancomycin and daptomycin were active against all Gram-positive strains tested, except the vancomycin-resistant strain *E. faecalis* V583, for which the vancomycin MIC was 32 mg/L and the daptomycin MIC was 4 mg/L. Compound 1 in combination with either vancomycin or daptomycin was within the range of variability as active against these test strains as the monosubstance Compound 1 (Table 2B).

TABLE 2B

Antibacterial activity (MIC in mg/L) of the monosubstances Compound 1, vancomycin, and daptomycin, or Compound 1 in combination with 0.5-times the MICs of vancomycin, and daptomycin.

| Strain | MCB | vanco | MCB + vanco | dapto | MCB + dapto |
|---|---|---|---|---|---|
| Sa ATCC29213 | 0.25 | 0.25 | 0.25 | 0.5 | 0.25 |
| Sa clone16 | 0.03 | 0.015 | 0.125 | 0.25 | 0.125 |
| Sa ATCC33593 | 0.03 | 0.5 | 0.125 | 1 | 0.125 |
| Sa NRS119 | 1 | 1 | 0.5 | 1 | 1 |
| Sa VisaMu50 | 0.06 | 2 | 0.25 | 2 | 0.25 |
| Ef ATCC29212 | 0.03 | 1 | 0.125 | 1 | 0.125 |
| Ef V583 | 0.03 | 32 | 0.06 | 4 | 0.06 |
| Efc DSMZ2146 | 0.06 | 0.25 | 0.125 | 1 | 0.125 |
| Efc UW3695 | 0.06 | 0.25 | 0.5 | 2 | 0.5 |
| Spn ATCC33400 | 0.0075 | 0.25 | 0.015* | 0.25 | 0.06 |
| Spn 19397 | 0.0004 | 0.25 | 0.0075* | 0.25 | 0.03 |

(MCB = Compound 1; vanco = vancomycin; dapto = daptomycin; Sa = *S. aureus*; Ef = *E. faecalis*; Efc = *E. faecium*; Spn = *S. pneumoniae*; *= these data were reproducible twice, but variable on the other occasion)

Moxifloxacin, Linezolid, Tigecycline:

Moxifloxacin exhibited good activity against most of the Gram-positive strains tested except *S. aureus* NRS-119 and Visa Mu 50, the linezolid- and quinolone-resistant *E. faecium* UW 3695, and the multidrug resistant *S. pneumoniae* 19397. Linezolid inhibited all the test strains except *S. aureus* NRS-119 and *E. faecium* UW 3695 at concentrations <4 mg/L. Tigecycline was active against all the test strains at concentrations <0.5 mg/L (Table 2C). Compound 1 in combination with moxifloxacin was as active as the monosubstance against the staphylococci ATCC 29213, clone 16, and ATCC 33593; however, Compound 1 gained activity against all the other test strains and the MICs were reduced to <0.000025 mg/L. Likewise, Compound 1 in combination with linezolid was as active as Compound 1 alone against the staphylococci ATCC 29213, clone 16, and ATCC 33593; however, Compound 1 gained activity against all the other test strains in combination with linezolid and the MICs were reduced to <0.000001 mg/L (except for the quinolone- and linezolid-resistant strain *E. faecalis* UW 3695 for which the combined MIC was 2 mg/L compared to 0.06 mg/L for Compound 1 alone) (Table 2C).

TABLE 2C

Antibacterial activity (MIC in mg/L) of the monosubstances Compound 1, moxifloxacin, linezolid, and tigecycline, or Compound 1 in combination with 0.5-times the MICs of moxifloxacin, linezolid, and tigecycline

| Strain | MCB | mox | MCB + mox | line | MCB + line | tige | MCB + tige |
|---|---|---|---|---|---|---|---|
| Sa ATCC29213 | 0.25 | 0.125 | 0.25 | 2 | 0.25 | 0.25 | 0.25 |
| Sa clone16 | 0.03 | 0.03 | 0.06 | 2 | 0.015 | 0.125 | 0.125 |
| Sa ATCC33593 | 0.03 | 0.06 | 0.06 | 2 | 0.0075 | 0.25 | 0.03 |
| Sa NRS119 | 1 | 8 | 0.125 | 64 | 0.06 | 0.25 | 1 |
| Sa VisaMu50 | 0.06 | 8 | <0.000025 | 4 | <0.000001 | 0.5 | 0.5 |
| Ef ATCC29212 | 0.03 | 0.5 | <0.000025 | 4 | <0.000001 | 0.25 | 0.25 |
| Ef V583 | 0.03 | 0.25 | <0.000025 | 2 | <0.000001 | 0.25 | 0.125 |
| Efc DSMZ2146 | 0.06 | 0.5 | <0.000025 | 4 | <0.000001 | 0.25 | 0.06 |
| Efc UW3695 | 0.06 | 64 | <0.000025 | 16 | 2 | 0.25 | 0.25 |
| Spn ATCC33400 | 0.0075 | 0.25 | <0.000025 | 2 | <0.000001 | 0.0075 | 0.125 |
| Spn 19397 | 0.0004 | 4 | <0.000025 | 1 | <0.000001 | 0.0075 | 0.003 |

(MCB = Compound 1; mox = moxifloxacin; line = linezolid; tige = tigecycline; Sa = *S. aureus*; Ef = *E. faecalis*; Efc = *E. faecium*; Spn = *S. pneumoniae*; * = these data were reproducible twice, but variable on the other occasion)

2.3 Time-Kill Curves of Compound 1 in the Presence of Colistin and Fosfomycin Time-dependent effects of Compound 1 in combination with colistin and fosfomycin on viable counts have been determined. Viable counts recorded at 8 hours are summarized in Tables 3A and 3B. Calculated kill rates are shown in Tables 4A and 4B. Strains E. coli ATCC 25922, NRZ-00401, NRZ-00302 and GNS-2601 were exposed to combinations of Compound 1 with colistin and fosfomycin, respectively, at once and twice their MICs. The following combinations of these agents were tested:

1×MIC Compound 1+1×MIC colistin or fosfomycin (1+1)
1×MIC Compound 1+2×MIC colistin or fosfomycin (1+2)
2×MIC Compound 1+1×MIC colistin or fosfomycin (2+1)
2×MIC Compound 1+2×MIC colistin or fosfomycin (2+2)

Compound 1 at one- or two-times its MICs exhibited a bacteriostatic activity during the first four to six hours against these Gram-negative test strains; thereafter, the strains regrew. Likewise, fosfomycin acted bacteriostatically against strains ATCC 25922, NRZ-00401, but was bactericidal against strains NRZ-00302, and GNS-2601, however, not eliminating the latter two strains out of the test system (Table 3A). Colistin was bactericidal against the four E. coli strains tested and reduced viable counts below the limit of detectability within six to eight hours (except strain NRZ-00302, which was markedly reduced within 8 hours, and eliminated within 24 hours) (Table 3B).

Compound 1 in combination with fosfomycin in 1+1 and 2+1 ratios was bacteriostatic against the strains ATCC 25922 and NRZ-00401, but prevented their regrowth in contrast to the exposition to Compound 1 alone. The 1+2 combination reduced viable counts of strain ATCC 25922 to 0.7 $\log_{10}$ CFU/mL at 8 hours, but a regrowth up 3.9 $\log_{10}$ CFU/mL was noted thereafter (Table 3A). The 2+2 combination eliminated the test strain E. coli ATCC 25922 out of system within 24 hours. Strain NRZ-00401 was affected bacteriostatically by the 1+1 and 1+2 combinations, the 1+2 combination reducing viable counts to 2.9 $\log_{10}$ CFU/mL within 8 hours, regrowing thereafter. Strains NRZ-00302 and GNS-2601 were eliminated out of the test system by any of the Compound 1+fosfomycin combination ratios tested within 24 hours.

TABLE 3A

Viable counts in $\log_{10}$ CFU/mL at 8 h of exposure to Compound 1 (MCB), fosfomycin (fosfo), or the combinations of the two agents at one-(1x) or two-times (2x) their MICs

| Agent | ATCC25922 | NRZ00401 | NRZ00302 | GNS2601 |
|---|---|---|---|---|
| Control | 9.06 | 8.95 | 8.99 | 8.29 |
| 1x MCB | 4.69 | 6.32 | 8.28 | 8.34 |
| 2x MCB | 2.61 | 4.26 | 5.69 | 6.29 |
| 1x fosfomycin | 8.95 | 7.95 | 2.78 | 5.08 |
| 2x fosfomycin | 8.59 | 6.65 | 1.30 | 3.45 |
| Combinations | | | | |
| 1MCB + 1fosfo | 3.31 | 4.36 | 0 | 1.70 |
| 1MCB + 2fosfo | 0.69 | 2.92 | 0 | 2.0 |
| 2MCB + 1fosfo | 2.44 | 3.66 | 0 | 1.65 |
| 2MCB + 2fosfo | 0.0 | 1.84 | 0 | 2.23 |

Any of the combinations of Compound 1 with colistin eliminated the strains out the test system within 24 h as did colistin alone (Table 3B).

TABLE 3B

Viable counts in $\log_{10}$ CFU/mL at 8 h of exposure to Compound 1 (MCB), colistin (col), or the combinations of the two agents at one-(1x) or two-times (2x) their MICs

| Agent | ATCC25922 | NRZ00401 | NRZ00302 | GNS2601 |
|---|---|---|---|---|
| Control | 9.06 | 8.95 | 8.99 | 9.29 |
| 1x MCB | 4.69 | 6.32 | 8.28 | 7.34 |
| 2x MCB | 2.62 | 0 | 5.69 | 6.29 |
| 1x colistin | 0 | 0 | 1.95 | 0 |
| 2x colistin | 0 | 0 | 0 | 0 |
| Combinations | | | | |
| 1MCB + 1col | 0 | 0 | 1.77 | 0 |
| 1MCB + 2col | 0 | 0 | 0 | 0 |
| 2MCB + 1col | 0 | 0 | 2.66 | 0 |
| 2MCB + 2col | 0 | 0 | 0 | 0 |

The augmented reduction of viable counts of the E. coli strains tested, in particular the increased activity of the Compound 1 plus fosfomycin combination, is reflected in an increased speed of reduction of viable counts, too. Data summarized in Tables 4A and 4B represent the kill-rates as calculated for the first four hours of exposure to the monosubstances or their combinations. Data summarized in Table 4A indicate that the monosubstances Compound 1 and fosfomycin alone reduced the growth rates of two out of the four test strains. The combinations of the two agents reduced viable counts at kill-rates ranging from 1.01 to 2.38 $h^{-1}$.

TABLE 4A

Effect of Compound 1 (MCB), fosfomycin (fosfo), or the combinations of the two agents at one-(1x) or two-times (2x) their MICs on the growth- and kill rates of four E. coli test strains, respectively.

| Agent | ATCC25922 | NRZ00401 | NRZ00302 | GNS2601 |
|---|---|---|---|---|
| Control | +1.06 | +1.03 | +1.01 | +1.22 |
| 1x MCB | 0.82 | +0.08 | +0.46 | +0.43 |
| 2x MCB | 1.35 | 0.25 | +0.25 | +0.35 |
| 1x fosfomycin | +0.68 | +0.40 | 1.67 | 1.21 |
| 2x fosfomycin | +0.72 | +0.32 | 2.09 | 1.85 |
| Combinations | | | | |
| 1MCB + 1fosfo | 1.96 | 1.12 | 2.27 | 1.94 |
| 1MCB + 2fosfo | 2.03 | 1.00 | 1.92 | 1.64 |
| 2MCB + 1fosfo | 1.97 | 1.22 | 2.38 | 1.76 |
| 2MCB + 2fosfo | 2.19 | 1.01 | 2.02 | 1.47 |

Positive values (marked with a '+') indicate growth, all the remainder values are negative and indicate the speed of reduction of viable counts, i.e. the kill rates $k(h^{-1})$ The pronounced bactericidal activity of colistin against the E. coli strains tested was not increased (except E. coli ATCC 25922) by the combination of colistin with Compound 1 (Table 4B).

TABLE 4B

Effects of Compound 1 (MCB), colistin (col), or the combinations of the two agents at one-(1x) or two-times (2x) their MICs on the growth- and kill rates of four E. coli test strains, respectively.

| Agent | ATCC25922 | NRZ00401 | NRZ00302 | GNS2601 |
|---|---|---|---|---|
| Control | +1.34 | +1.03 | +1.01 | +1.21 |
| 1x MCB | 0.74 | 0.09 | +0.45 | +0.43 |
| 2x MCB | 1.62 | 0.25 | +0.25 | +0.35 |
| 1x colistin | 0.86 | 2.46 | 1.63 | 1.55 |
| 2x colistin | 1.04 | 2.53 | 1.89 | 1.80 |
| Combinations | | | | |
| 1MCB + 1col | 2.29 | 1.99 | 1.60 | 1.52 |
| 1MCB + 2col | 2.31 | 2.27 | 1.24 | 1.83 |
| 2MCB + 1col | 2.24 | 2.06 | 0.98 | 1.04 |
| 2MCB + 2col | 2.29 | 2.42 | 1.94 | 1.09 |

Positive values (marked with a '+') indicate growth, all the remainder values are negative and indicate the speed of reduction of viable counts, i.e. the kill rates $k(h^{-1})$

2.4 Checkerboard Titrations of Compound 1 and Colistin

The checkerboard titrations were performed three times. Each concentration of Compound 1 ranging from <0.015 to 256 mg/L has been combined with every concentration of colistin ranging from <0.015 to 256 mg/L.

The test strains E. coli ATCC 25922 (susceptible reference strain), E. coli NRZ-00302 (NDM-1 β-lactamase), K. pneumoniae NRZ-00535 (VIM-1 β-lactamase), P. aeruginosa NRZ-00425 (VIM-2 β-lactamase), E. cloacae ATCC 13047 (susceptible reference strain), and E. cloacae NRZ-00239 (VIM-1 β-lactamase) were exposed to each and every concentrations of Compound 1 and colistin.

In general, the MICs of Compound 1 fell below 0.015 mg/L in combination with two- or at least four-times the colistin MICs, while a combination of colistin concentrations lower than 0.25-times its MIC had no effect on the MICs of Compound 1 for most of the strains tested except E. cloacae ATCC 13047. E. cloacae ATCC 13047 was resistant to colistin with a MIC of 256 mg/L; combinations of Compound 1 with a colistin concentration of 128 mg/L resulted in a decrease of the MICs of Compound 1 from >256 mg/L to 1-0.5 mg/L; even a colistin concentration as low as 2 mg/L reduced the MIC of Compound 1 to 1-4 mg/L.

The data summarized in Table 5 represent the combination effect on the MICs of Compound 1 in the presence of one subinhibitory (i.e. 0.5-times the MIC), one inhibitory (i.e. 1.0-times the MIC), and two suprainhibitory concentration (i.e. 2.0-times and 4.0-times the MIC) of colistin.

Data summarized in Table 5 indicate that inhibitory and suprainhibitory colistin concentrations reduce the MICs of Compound 1 from >256 mg/L to <0.015 mg/L. The FIC indices ranged from 0.5 to 1.8 for combinations of Compound 1 with subinhibitory colistin concentrations, from 1.0 to 2.0 for inhibitory and from 2.0 to 4.0 for suprainhibitory colistin concentrations.

TABLE 5

Checkerboard titrations of Compound 1 in combination with colistin against six selected indicator strains.

| Parameter | Ec ATCC | Ec NRZ | Kpn NRZ | Pa NRZ | Ecl ATCC | Ecl NRZ |
|---|---|---|---|---|---|---|
| MCB MIC | 8-16 | 256 | 256 | 128-256 | 256 | 256 |
| col MIC | 1-2 | 0.5-1 | 0.5-2 | 2 | 256 | 0.5-1 |
| MCB+0.5col | 0.125-4 | 256 | 256 | 256 | 0.5-1 | >256 |
| MCB+1.0col | 0.015-0.06 | 0.015-32 | 0.015-256 | 64-256 | 0.125-0.5 | 256 |
| MCB+2.0col | <0.015 | <0.015 | 0.015-256 | 0.015-0.06 | not tested* | 0.015-256 |
| MCB+4.0col | <0.015 | <0.015 | <0.015 | <0.015 | not tested* | <0.015 |
| FICind0.5col | 0.6 | 1.5 | 1.5 | 1.8 | 0.5 | not calcul. |
| FICind1.0col | 1.0 | 1.0 | 1.5 | 1.7 | 1.0 | 2.0 |
| FICind2.0col | 2.0 | 2.0 | 2.5 | 2.0 | not tested* | 2.3 |
| FICind4.0col | 4.0 | 4.0 | 4.0 | 4.0 | not tested* | 4.0 |

The following strains have been tested:
E. coli ATCC 25922 (EcATCC); E. coli NRZ-00302 (Ec NRZ), K. pneumoniae NRZ-00535 (kpn NRZ), P. aeruginosa NRZ-00425 (Pa NRZ), E. cloacae ATCC 13047 (Ecl ATCC), and E. cloacae NRZ-00239 (Ecl NRZ).
(Parameters: MICs in mg/L; MCB MIC = MIC of Compound 1; col MIC = MIC of colistin; MCB+0.5col = MIC of Compound 1 in the presence of 0.5-times the colistin MIC; MCB+1.0col = MIC of Compound 1 in the presence of 1.0-times the colistin MIC; MCB+2.0col = MIC of Compound 1 in the presence of 2.0-times the colistin MIC; MCB+4.0col = MIC of Compound 1 in the presence of 4.0-times the colistin MIC; FICind0.5col = FIC index in the presence of 0.5-times the colistin MIC; FICind1.0col = FIC index in the presence of 1.0-times the colistin MIC; FICind2.0col = FIC index in the presence of 2.0-times the colistin MIC; FICind4.0col = FIC index in the presence of 4.0-times the colistin MIC; the FIC indices represent the mean from two or three tests or the result of a single test)
*As the colistin MIC was 256 mg/L, combinations of Compound 1 with two- and four-times the colistin MIC were not tested because of limited solubility of colistin

3. Discussion

3.1 Combination of Compound 1 with Colistin and Fosfomycin

Colistin and fosfomycin have been tested in combination with Compound 1 against selected Gram-negative bacteria producing different types of β-lactamases; production of extended spectrum β-lactamases (ESBLs) is frequently associated with multidrug resistance. The increasing prevalence of multidrug resistant bacteria reduces treatment options, so that the development of novel agents and/or the use of combinations of antibacterial agents may offer a solution for this problem. Selected Gram-negative bacteria producing ESBLs (e.g. CTX-M-15, VIM, NDM-1) were exposed to Compound 1 in combination with colistin, and in some experiments to Compound 1 in combination with fosfomycin.

It is evident from the data reported in Section 2.2 that subinhibitory concentrations of both colistin and fosfomycin did not increase the susceptibilities of the test strains to Compound 1, as the MICs of Compound 1 for the test strains were not reduced (Table 1A).

As in this first series of experiments only one subinhibitory concentration of colistin or fosfomycin has been combined with various concentrations of Compound 1, the checkerboard method has been applied to combinations of Compound 1 and colistin (see Section 2.4). This method results in the exposition of each test strain to each and every concentration of the two combination agents, i.e. Compound 1 and colistin. The parameter being generally accepted as an indicator for synergism, additive effects, indifference, and antagonism is the FIC index. Synergism is defined as an FIC index of less than 0.5. Additive or indifferent effects are defined as an FIC index of 0.5-4 (additive >0.5-1; indifferent >1-4). Antagonism was defined as an FIC index of more than 4 (Terminology relating to methods for the determination of susceptibility of bacteria to antimicrobial agents. European Committee for Antimicrobial Susceptibility testing (EUCAST) of the European Society for Clinical Microbiology and Infectious Diseases (ESCMID). EUCAST definitive document E.Def 1.2; Clin Microbiol Infect Dis 2000; 6:503-508). Data summarized in Table 5 demonstrate that for all strains exposed to Compound 1 plus 0.5- or two-times the colistin MICs, the FIC indices ranged from 0.5 to 2.5, thus indicating indifference.

However, the FIC indices should be interpreted with caution: For example, a mean FIC index of 2.0 and 2.3 has been calculated for $E.$ $cloacae$ NRZ-00239 for the combination of Compound 1 with one- and two-times the colistin MIC, respectively. This is due to the fact that, e.g., in one of the experiments the colistin MIC amounted to 1 mg/L and the MIC of Compound 1 to 256 mg/L, so that the FIC index for the 1 mg/L colistin plus 256 mg/L Compound 1 combination is 2.0 (=(1/1)+(256/256)) indicating indifference. However, exposition of this test strain to two-times the colistin MIC plus Compound 1 in another experiment resulted in a marked increase in its susceptibility to Compound 1 which is mirrored by a Compound 1 MIC-value of <0.015 mg/L. The FIC index for this combination of 2 mg/L colistin plus 0,015 mg/L Compound 1 is 2.00006 (=(2/1)+(0.015/256)), i.e. not different from above and indicating indifference, too. The FIC index for the combination of 4 mg/L colistin plus 0.015 mg/L Compound 1 is even 4. This example demonstrates that the calculation of FIC indices is not consistent with the definition of synergism, addition, indifference or antagonism. Although the checkerboard technique and the calculation of FIC indices are routinely used for evaluation of combination testing, this method has significant limitations: It yields only data quantitating the inhibitory but not bactericidal activity, and provides only an all-or-none response (i.e. growth or no growth) but no graded responses quantitating reductions of viable counts. Most importantly, the calculation of FIC indices assumes incorrectly that all combination partners exhibit a linear concentration response (Pillai S K, Moellering R C, Eliopoulos G M. Antimicrobial combinations. In: Antibiotics in Laboratory Medicine. Lorian V (Ed.), chapter 9, 5$^{th}$ edition, 2005, Lippincrott Raven). A linear concentration-activity response has been demonstrated for colistin, fluoroquinolones and aminoglycosides but not for β-lactams or Compound 1. Therefore, FIC indices have only a limited predictive value for the characterization of combination effects of Compound 1 with other agents. The marked reduction of Compound 1 MICs from 256 mg/L to <0.015 mg/L for five of the strains tested and from 8-16 mg/L to <0.015 mg/L for the $E.$ $coli$ ATCC 25922 strain in combination with two- to four-times the colistin MICs, and at the same time yielding FIC indices from 0.6 to 4.0, demonstrate that the calculation of FIC indices is not the adequate procedure to describe these combination effects.

This fact is corroborated by the finding that although the FIC indices indicate indifference, kill curve experiments revealed that Compound 1 showing low activity against Gram-negatives as a monosubstance exhibited bactericidal activity against the Gram-negative test strains in the presence of one- and two-times the MICs of colistin or fosfomycin (see Section 5.3). The combination of Compound 1 plus either colistin or fosfomycin reduced viable counts and eliminated the test strains out of the system more rapidly than either agent alone (Tables 3A, 3B and 4A, 4B). The finding that inhibitory and suprainhibitory concentrations of colistin or fosfomycin enhance the activity of Compound 1 against these Gram-negative indicator strains is also mirrored by the fact that the Compound 1 MICs were reduced from e.g. 256 mg/L to values as low as <0.015 mg/L in the checkerboard titrations. Thus, inhibitory and suprainhibitory concentrations of colistin reduce the Compound 1 MICs. This finding could be explained by the fact that polymyxins are known to increase the permeability of the outer membrane of Gram-negatives (Vaara M. Agents that increase the permeability of the outer membrane. Microbiol Rev 1992; 56 (3): 395-411) thus reducing the MICs of otherwise less active agents. However, the finding of this study that Compound 1 concentrations corresponding to one-times its MIC increased the bactericidal potency of colistin is unexpected.

Thus, the combination of Compound 1 and colistin gained bactericidal activity making antibacterial therapy more effective. In addition, it is important to note that antagonistic effects were not recorded, so that a combination of Compound 1 with colistin extends the Gram-positive antibacterial spectrum of Compound 1 significantly to Gram-negative pathogens including difficult to treat, multidrug resistant strains.

3.2 Combination of Compound 1 with Combination Agents Effects on Gram-Negative Bacteria:

Combinations of Compound 1 with antibacterial agents other than colistin or fosfomycin used clinically in the treatment of infections due to Gram-negative pathogens yielded indifferent results (see Section 2.2, Tables 1B and 1C), indicating that Compound 1 can probably be combined with 9-lactams, aminoglycosides, fluoroquinolones or tigecycline to treat patients empirically.

Effects on Gram-Positive Bacteria:

The combination of Compound 1 with ampicillin or ceftriaxone at 0.5-times their MICs reduced on the one hand the Compound 1 MICs for the three MRSA indicator strains, but on the other hand not for the MSSA test strains (Section 2.2., Table 2A). This finding is unexpected as the β-lactam target in the MRSA strains, the penicillin-binding protein two, has been mutated towards a very low β-lactam affinity. The same holds true for the combination effect of Compound 1 plus ceftriaxone against *S. pneumoniae* BAY 19397. Again, the susceptible reference strain was not affected by this combination. It seems to be rather unlikely that exposition to Compound 1 restores the affinity of the target to β-lactams. Therefore, the finding generated in this study that subinhibitory ampicillin- or ceftriaxone-concentrations in combination with Compound 1 act synergistically against MRSA and β-lactam-resistant streptococci and enterococci was unexpected. The combination of Compound 1 with β-lactams restores the efficacy of β-lactams in the therapy of methicillin- or penicillin-resistant staphylococci, streptococci and enterococci.

The combinations of Compound 1 with vancomycin or daptomycin (Section 2.2., Table 2B) or tigecycline (Table 2C) yielded indifferent results.

The combinations of Compound 1 with either moxifloxacin or linezolid was highly synergistic, reducing the Compound 1 MICs for most of the strains to <0.000025 mg/L (Section 2.2., Table 2C). Thus, the combination of Compound 1 with either moxifloxacin or linezolid apparently restores their activity against quinolone- or oxazolidinone-resistant bacteria and augments the activity of both combination partners against these difficult to treat Gram-positive MDR isolates.

From the data given above it can be concluded that:

1. Colistin significantly enhances the activity of Oxazolidinone-quinolone hybrids (such as Compound 1) against Gram-negative bacteria extending the antibacterial spectrum of Oxazolidinone-quinolone hybrids (such as Compound 1) to Gram-negatives including difficult to treat MDR strains.

2. Due to indifferent or synergistic combination effects Oxazolidinone-quinolone hybrids (such as Compound 1) may be combined with other commercially available antibacterials used in the treatment of Gram-negative pathogens to complement the predominantly Gram-positive spectrum of Oxazolidinone-quinolone hybrids (such as Compound 1) in initial empirical treatment of bacterial infections.

3. A highly synergistic effect against MRSA and MDR-pneumococci or MDR-enterococci was observed for the combination of Oxazolidinone-quinolone hybrids (such as Compound 1) with β-lactams or moxifloxacin and linezolid, thus enhancing the activity of Oxazolidinone-quinolone hybrids (such as Compound 1), and probably restoring the activity of β-lactams or moxifloxacin and linezolid.

The invention claimed is:

1. A combination of:
   i) at least one oxazolidinone-quinolone hybrid which is selected from the following compounds:

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-[1,8]naphthyridine-3-carboxylic acid:

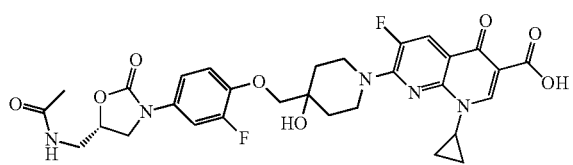 [SMILES: CC(=O)NC[C@H]1CN(c2ccc(OCC3(O)CCN(c4nc5c(cc4F)c(=O)c(C(=O)O)cn5C4CC4)CC3)c(F)c2)C(=O)O1]

7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-[1,8]naphthyridine-3-carboxylic acid:

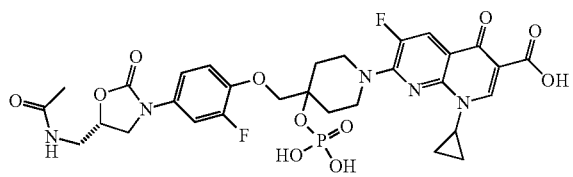 [SMILES: CC(=O)NC[C@H]1CN(c2ccc(OCC3(OP(=O)(O)O)CCN(c4nc5c(cc4F)c(=O)c(C(=O)O)cn5C4CC4)CC3)c(F)c2)C(=O)O1]

7-[4-{4-[(5S)-5-(acetylamino-methyl)-2-oxo-oxazolidin-3-yl]-2-fluoro-phenoxymethyl}-4-(2,6-diamino-hexanoyloxy)-piperidin-1-yl]-1-cyclopropyl-6-fluoro-4-oxo-1,4-dihydro-[1,8]naphthyridine-3-carboxylic acid:

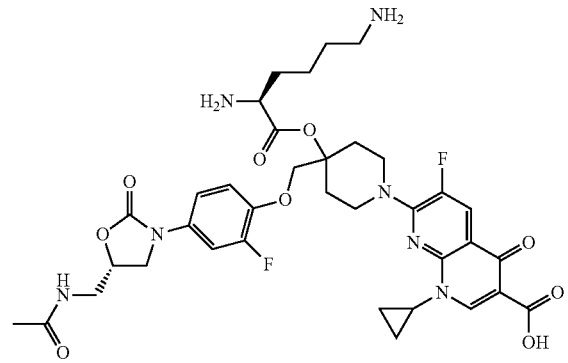 [SMILES: CC(=O)NC[C@H]1CN(c2ccc(OCC3(OC(=O)[C@@H](N)CCCCN)CCN(c4nc5c(cc4F)c(=O)c(C(=O)O)cn5C4CC4)CC3)c(F)c2)C(=O)O1]

51

Succinic acid mono-[4-{4-[(5S)-5-(acetylamino-methyl)-2-oxo-oxazolidin-3-yl]-2-fluoro-phenoxymethyl}-1-(6-carboxy-8-cyclopropyl-3-fluoro-5-oxo-5,8-dihydro-[1,8]naphthyridin-2-yl)-piperidin-4-yl] ester:

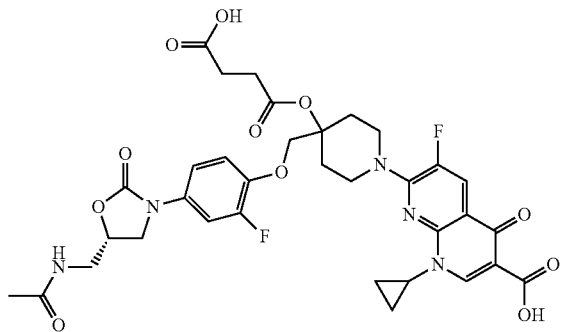 [SMILES: CC(=O)NC[C@H]1CN(c2ccc(OCC3(OC(=O)CCC(=O)O)CCN(c4nc5c(cc4F)c(=O)c(C(=O)O)cn5C4CC4)CC3)c(F)c2)C(=O)O1]

52

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

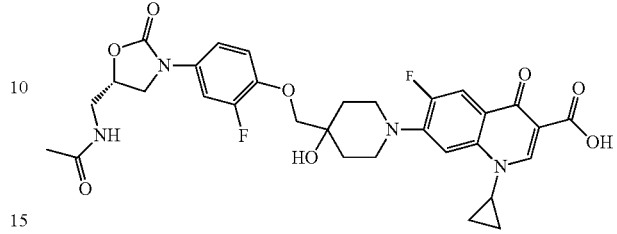

7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

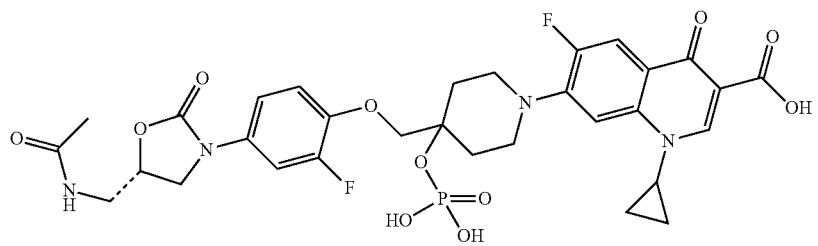 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-8-methoxy-4-oxo-1,4-dihydro-quinoline-3-carboxylic acid:

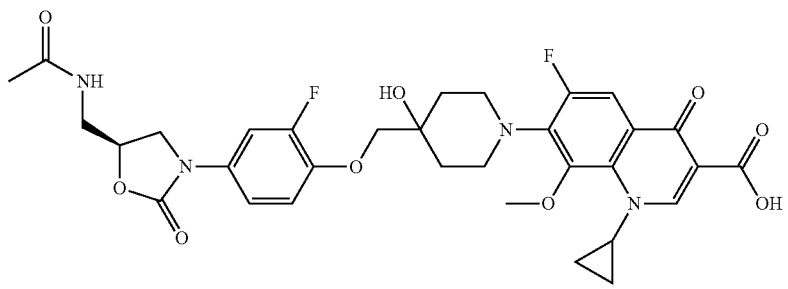

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-8-methoxy-4-oxo-1,4-dihydro-quinoline-3-carboxylic acid:

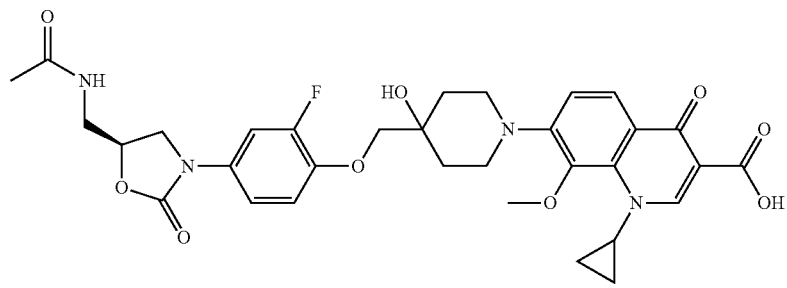 [SMILES: COc1c(N2CCC(O)(COc3ccc(N4C[C@H](CNC(C)=O)OC4=O)cc3F)CC2)ccc2c(=O)c(C(=O)O)cn(C3CC3)c12]

9-(4-{4-[(5S)-5-(acetylamino-methyl)-2-oxo-oxazolidin-3-yl]-2-fluoro-phenoxymethyl}-4-hydroxy-piperidin-1-yl)-8-fluoro-3-methyl-6-oxo-2,3-dihydro-6H-1-oxa-3a-aza-phenalene-5-carboxylic acid:

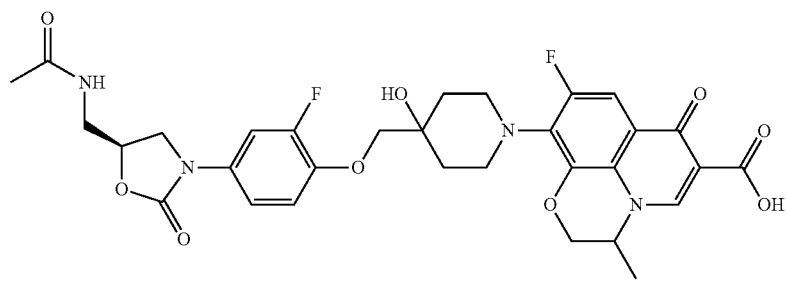 [SMILES: CC(=O)NC[C@H]1CN(c2ccc(OCC3(O)CCN(c4c(F)cc5c(=O)c(C(=O)O)cn6c5c4OCC6C)CC3)c(F)c2)C(=O)O1]

7-(3-{4-[(5S)-5-(acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-[1,8]naphthyridine-3-carboxylic acid:

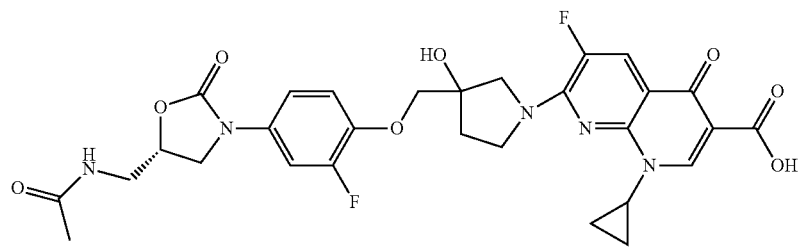 [SMILES: CC(=O)NC[C@H]1CN(c2ccc(OCC3(O)CCN(c4nc5c(cc4F)c(=O)c(C(=O)O)cn5C4CC4)C3)c(F)c2)C(=O)O1]

7-(3-{4-[(5S)-5-(acetylamino-methyl)-2-oxo-oxazolidin-3-yl]-2-fluoro-phenoxymethyl}-3-hydroxy-pyrrolidin-1-yl)-1-cyclopropyl-6-fluoro-4-oxo-1,4-dihydro-quinoline-3-carboxylic acid:

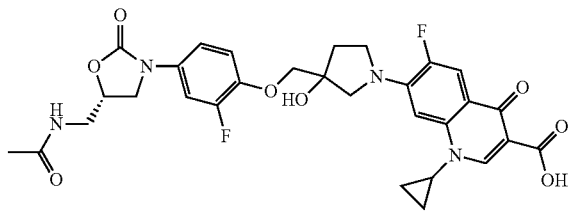 [SMILES: CC(=O)NC[C@H]1CN(c2ccc(OCC3(O)CCN(c4cc5c(cc4F)c(=O)c(C(=O)O)cn5C4CC4)C3)c(F)c2)C(=O)O1]

7-(3-{4-[(5S)-5-(acetylamino-methyl)-2-oxo-oxazolidin-3-yl]-2-fluoro-phenoxymethyl}-3-hydroxy-pyrrolidin-1-yl)-1-cyclopropyl-6-fluoro-8-methoxy-4-oxo-1,4-dihydro-quinoline-3-carboxylic acid:

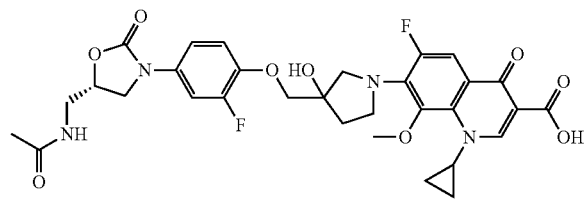 [SMILES: COc1c(N2CCC(O)(COc3ccc(N4C[C@H](CNC(C)=O)OC4=O)cc3F)C2)c(F)cc2c(=O)c(C(=O)O)cn(C3CC3)c12]

7-(3-{4-[(5S)-5-(acetylamino-methyl)-2-oxo-oxazolidin-3-yl]-2-fluoro-phenoxymethyl}-3-hydroxy-pyrrolidin-1-yl)-1-cyclopropyl-8-methoxy-4-oxo-1,4-dihydro-quinoline-3-carboxylic acid:

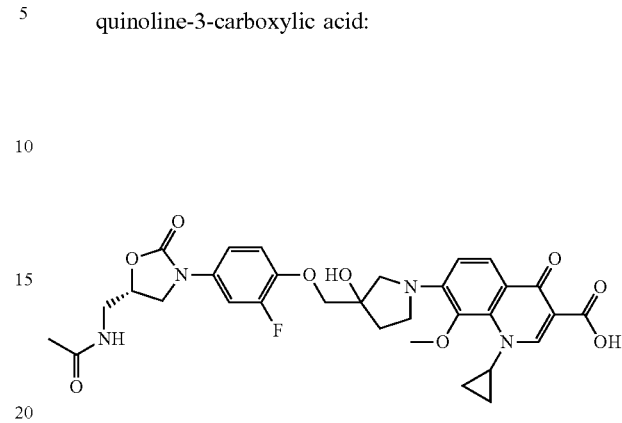

9-(3-{4-[(5S)-5-(acetylamino-methyl)-2-oxo-oxazolidin-3-yl]-2-fluoro-phenoxymethyl}-3-hydroxy-pyrrolidin-1-yl)-8-fluoro-3-methyl-6-oxo-2,3-dihydro-6H-1-oxa-3a-aza-phenalene-5-carboxylic acid:

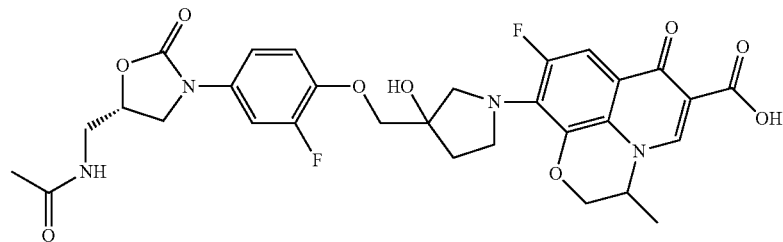 [SMILES: CC(=O)NC[C@H]1CN(c2ccc(OCC3(O)CCN(c4c(F)cc5c(=O)c(C(=O)O)cn6c5c4OCC6C)C3)c(F)c2)C(=O)O1]

7-(4-{4-[(5S)-5-(acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-quinoline-3-carboxylic acid:

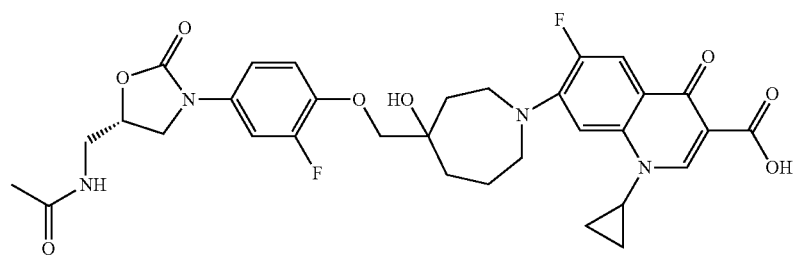 [SMILES: CC(=O)NC[C@H]1CN(c2ccc(OCC3(O)CCCN(c4cc5c(cc4F)c(=O)c(C(=O)O)cn5C4CC4)CC3)c(F)c2)C(=O)O1]

7-(4-{4-[(5S)-5-(acetylamino-methyl)-2-oxo-oxazolidin-3-yl]-2-fluoro-phenoxymethyl}-4-hydroxy-azepan-1-yl)-1-cyclopropyl-6-fluoro-4-oxo-1,4-dihydro-[1,8]naphthyridine-3-carboxylic acid:

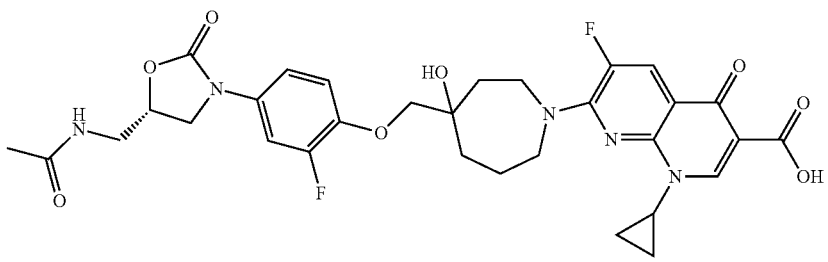 [SMILES: CC(=O)NC[C@H]1CN(c2ccc(OCC3(O)CCCN(c4nc5c(cc4F)c(=O)c(C(=O)O)cn5C4CC4)CC3)c(F)c2)C(=O)O1]

sodium salt of 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid;

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-quinoline-3-carboxylic acid:

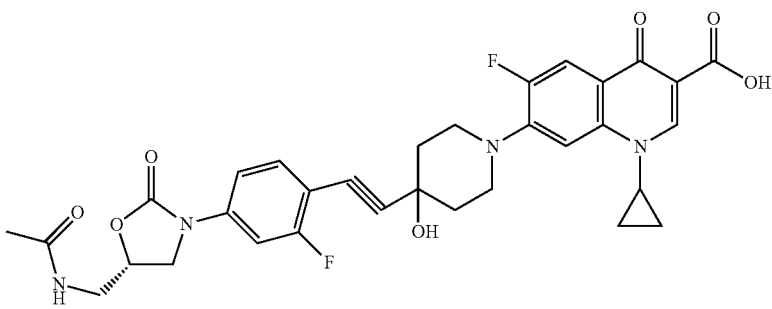 [SMILES: CC(=O)NC[C@H]1CN(c2ccc(C#CC3(O)CCN(c4cc5c(cc4F)c(=O)c(C(=O)O)cn5C4CC4)CC3)c(F)c2)C(=O)O1]

7-(4-{4-[5S-(acetylamino-methyl)-2-oxo-oxazolidin-3-yl]-2-fluoro-phenylethynyl}-4-hydroxy-piperidin-1-yl)-1-cyclopropyl-6-fluoro-4-oxo-1,4-dihydro-[1,8]-napthyridine-3-carboxylic acid:

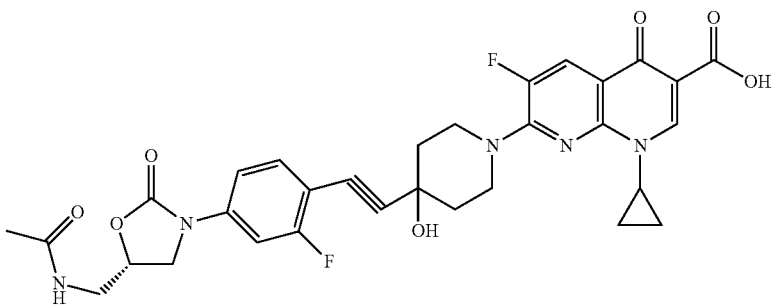 [SMILES: CC(=O)NC[C@H]1CN(c2ccc(C#CC3(O)CCN(c4nc5c(cc4F)c(=O)c(C(=O)O)cn5C4CC4)CC3)c(F)c2)C(=O)O1]

7-[4-(2-{4-[5S-(acetylamino-methyl)-2-oxo-oxazolidin-3-yl]-2-fluoro-phenyl}-ethyl)-4-hydroxy-piperidin-1-yl]-1-cyclopropyl-6-fluoro-4-oxo-1,4-dihydro-quinoline-3-carboxylic acid:

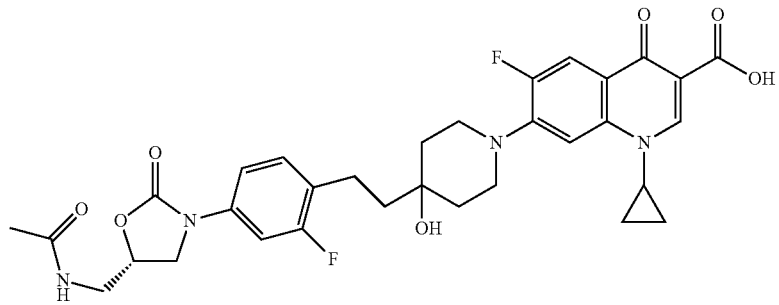 [SMILES: CC(=O)NC[C@H]1CN(c2ccc(CCC3(O)CCN(c4cc5c(cc4F)c(=O)c(C(=O)O)cn5C4CC4)CC3)c(F)c2)C(=O)O1]

and 1-cyclopropyl-6-fluoro-7-[4-({2-fluoro-4-[(5R)-5-(hydroxymethyl)-2-oxo-1,3-oxazolidin-3-yl]phenoxy}methyl)-4-hydroxypiperidin-1-yl]-4-oxo-1,4-dihydroquinolin-3-carboxylic acid:

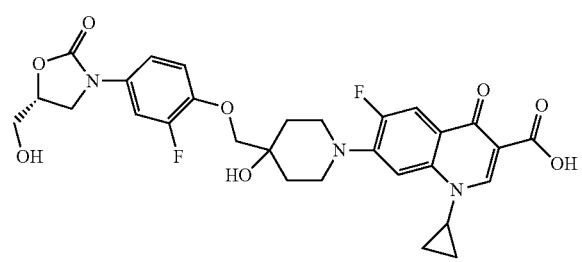 [SMILES: O=C(O)c1cn(C2CC2)c2cc(N3CCC(O)(COc4ccc(N5C[C@H](CO)OC5=O)cc4F)CC3)c(F)cc2c1=O]

or a pharmacologically acceptable salt, solvate or hydrate thereof; and ii) at least one further antibacterial compound which is different from compound (i) and selected from the following:

ceftriaxone, ampicillin, fosfomycin, polypeptides, linezolid and moxifloxacin.

2. The combination according to claim 1 wherein the at least one oxazolidinone-quinolone hybrid is selected from the following compounds:

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

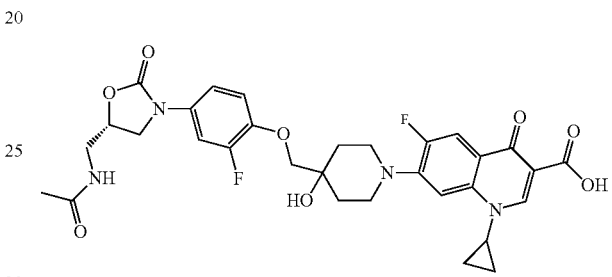

and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

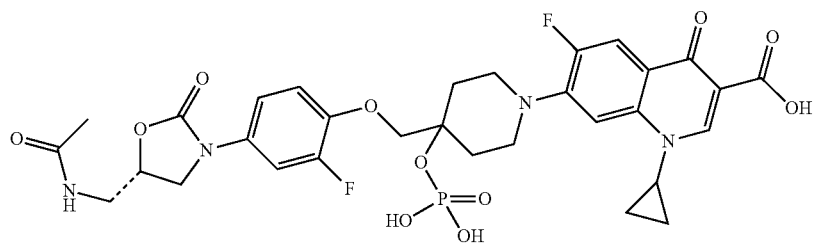 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a salt, solvate or hydrate thereof.

3. The combination according to claim 1 wherein the at least one further antibacterial compound (ii) is selected from the following compounds: colistin, fosfomycin, ampicillin, ceftriaxone, moxifloxacin and linezolid.

4. A combination of:

i) at least one oxazolidinone-quinolone hybrid which is selected from the following compounds:

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

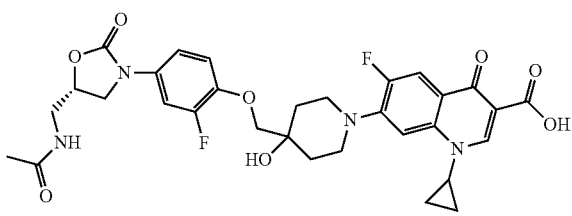 [SMILES: CC(=O)NC[C@H]1CN(c2ccc(OCC3(O)CCN(c4cc5c(cc4F)c(=O)c(C(=O)O)cn5C4CC4)CC3)c(F)c2)C(=O)O1]

and
7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

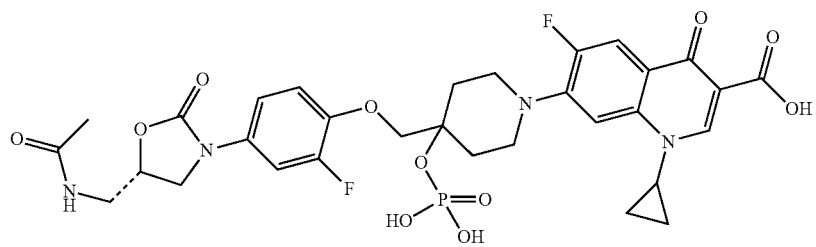 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a salt, solvate or hydrate thereof; and ii) at least one further antibacterial compound which is selected from the following compounds: colistin, fosfomycin, ampicillin, ceftriaxone, moxifloxacin and linezolid.

5. A pharmaceutical composition comprising a combination according to claim 1 and a carrier and/or diluent and/or adjuvant.

6. A kit-of-parts comprising:

i) at least one oxazolidinone-quinolone hybrid according to claim 1 and ii) at least one further antibacterial compound which is different from compound (i) according to claim 1.

7. A method for treating a subject suffering from a bacterial infection, comprising administering to the subject a combination according to claim 1.

8. A method for treating a subject suffering from a bacterial infection, comprising administering to the subject a pharmaceutical composition according to claim 5.

9. A method for treating a subject suffering from a bacterial infection, comprising administering to the subject a kit-of-parts according to claim 6.

10. A kit-of-parts comprising:

i) at least one oxazolidinone-quinolone hybrid which is selected from the following compounds:

7-(4-{4-[(5S)-5-(acetylamino-methyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid:

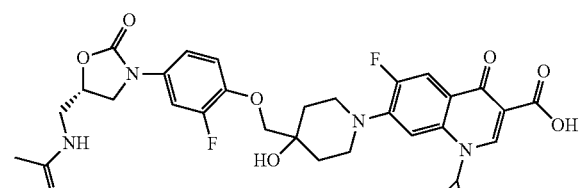

and 7-(4-{4-[(5S)-5-(acetylamino-methyl)-2-oxo-oxazolidin-3-yl]-2-fluoro-phenoxymethyl}-4-phosphonooxy-piperidin-1-yl)-1-cyclopropyl-6-fluoro-4-oxo-1,4-dihydro-quinoline-3-carboxylic acid:

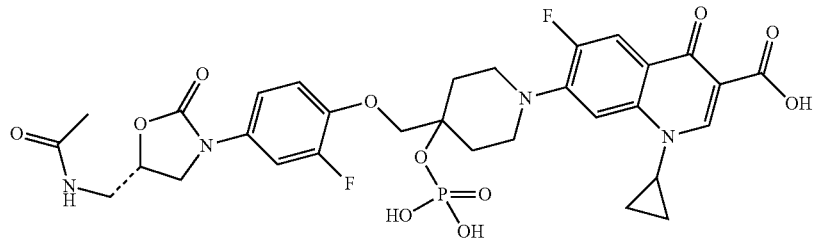 [SMILES: CC(=O)NC[C@H]1CN(c2ccc(OCC3(OP(=O)(O)O)CCN(c4cc5c(cc4F)c(=O)c(C(=O)O)cn5C4CC4)CC3)c(F)c2)C(=O)O1]

or a salt, solvate or hydrate thereof; and ii) at least one further antibacterial compound which is selected from the following compounds: colistin, fosfomycin, ampicillin, ceftriaxone, moxifloxacin and linezolid.

11. A method for treating a subject suffering from a bacterial infection, comprising administering to the subject a combination according to claim 4.

12. A pharmaceutical composition comprising a combination according to claim 4 and a carrier and/or diluent and/or adjuvant.

13. A method for treating a subject suffering from a bacterial infection, comprising administering to the subject a pharmaceutical composition according to claim 12.

14. A method for treating a subject suffering from a bacterial infection, comprising administering to the subject a kit-of-parts according to claim 10.

\* \* \* \* \*